United States Patent
Himmelsbach et al.

(10) Patent No.: US 6,653,305 B2
(45) Date of Patent: *Nov. 25, 2003

(54) BICYCLIC HETEROCYCLES, PHARMACEUTICAL COMPOSITIONS CONTAINING THEM, THEIR USE, AND PROCESSES FOR PREPARING THEM

(75) Inventors: Frank Himmelsbach, Mittelbiberach (DE); Elke Langkopf, Warthausen (DE); Birgit Jung, Schwabenheim (DE); Stefan Blech, Warthausen (DE); Flavio Solca, Vienna (AT)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/929,931

(22) Filed: Aug. 15, 2001

(65) Prior Publication Data

US 2002/0077330 A1 Jun. 20, 2002

Related U.S. Application Data

(60) Provisional application No. 60/230,389, filed on Sep. 6, 2000.

(30) Foreign Application Priority Data

Aug. 26, 2000 (DE) .......................... 100 42 060

(51) Int. Cl.⁷ .................. A61K 31/535; A61K 31/517; A61P 43/00; C07D 295/02; C07D 239/00
(52) U.S. Cl. ................. 514/233.5; 514/255; 514/266.1; 514/266.4; 514/312; 544/107; 544/253; 544/363
(58) Field of Search ............. 514/233.5, 255, 514/266.1, 266.4, 312; 544/107, 253, 363

(56) References Cited

U.S. PATENT DOCUMENTS 6,344,459 B1 * 2/2002 Bridges et al. .......... 514/234.5

FOREIGN PATENT DOCUMENTS

| DE | 19911509 A1 | 9/2000 |
|---|---|---|
| DE | 19928281 A1 | 12/2000 |
| DE | 100 17 539 A1 | 10/2001 |
| WO | WO 9909016 A1 | 2/1999 |
| WO | WO 0051991 A1 | 9/2000 |
| WO | WO 0055141 A1 | 9/2000 |

OTHER PUBLICATIONS

Tsou, Hwei–ru et al; 6–substituted–4–(3–bromophenylamino)quinazolines as Putative Irreversible Inhibitors of the Epidermal Growth Factor Receptor (EGFR) and Human Epidermal Growth Factor Receptor (HER–2) Tyrosine Kinases with Enhanced Antitumor Activity; J. Med Chem; 2001; V 44; Tsou . . . (continuation of above) pp. 2719–2734.

* cited by examiner

Primary Examiner—Mukund J. Shah
Assistant Examiner—Tamthom N. Truong
(74) Attorney, Agent, or Firm—R. P. Raymond; T. X. Witkowski

(57) ABSTRACT

A compound of formula (I)

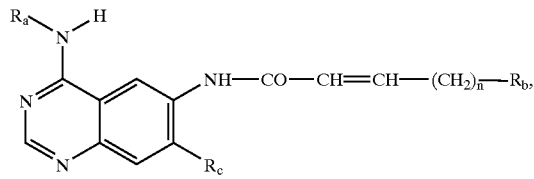

wherein:

$R_a$ is a benzyl or 1-phenylethyl group or a phenyl group substituted by the groups $R_1$ and $R_2$, wherein:
  $R_1$ is a hydrogen, fluorine, chlorine, or bromine atom, or a methyl, trifluoromethyl, cyano, or ethynyl group, and
  $R_2$ is a hydrogen or fluorine atom;

$R_b$ is an $R_3O$—CO—$CH_2$—N—$CH_2$—$CH_2$—OH group optionally substituted at the methylene groups by 1 or 2 methyl or ethyl groups, wherein $R_3$ is a hydrogen atom or a $C_{1-4}$-alkyl group, a 2-oxomorpholin-4-yl group optionally substituted by 1 or 2 methyl or ethyl groups, or a N-[(1,3-dioxolan-2-yl)methyl] methylamino group;

$R_c$ is a hydrogen atom, or a methoxy, ethoxy, 2-methoxyethoxy, 2-ethoxyethoxy, cyclobutyloxy, cyclopentyloxy, cyclohexyloxy, cyclopropylmethoxy, cyclobutylmethoxy, cyclopentylmethoxy, cyclohexylmethoxy, tetrahydrofuran-3-yloxy, tetrahydropyran-3-yloxy, tetrahydropyran-4-yloxy, tetrahydrofuranylmethoxy, or tetrahydropyranylmethoxy group; and n is 1, 2, or 3, the tautomers, stereoisomers, and salts thereof, particularly the physiologically acceptable salts thereof with inorganic or organic acids or bases which have valuable pharmacological properties, their use in the treatment of diseases, especially tumoral diseases and diseases of the lungs and airways, and the preparation thereof.

8 Claims, No Drawings

BICYCLIC HETEROCYCLES, PHARMACEUTICAL COMPOSITIONS CONTAINING THEM, THEIR USE, AND PROCESSES FOR PREPARING THEM

The present invention relates to bicyclic heterocycles of general formula

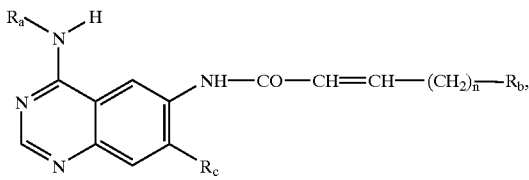

the tautomers, the stereoisomers, and the salts thereof, particularly the physiologically acceptable salts thereof with inorganic or organic acids or bases which have valuable pharmacological properties, particularly an inhibitory effect on signal transduction mediated by tyrosine kinases, the use thereof for treating diseases, particularly tumoral diseases, diseases of the lungs and respiratory tract, and the preparation thereof.

In the above general formula I $R_a$ denotes a benzyl or 1-phenylethyl group or a phenyl group substituted by the groups $R_1$ and $R_2$, where
  $R_1$ denotes a hydrogen, fluorine, chlorine, or bromine atom, or a methyl, trifluoromethyl, cyano, or ethynyl group, and
  $R_2$ denotes a hydrogen or fluorine atom, $R_b$ denotes an $R_3O$—CO—$CH_2$—N—$CH_2$—$CH_2$—OH group optionally substituted at the methylene groups by 1 or 2 methyl or ethyl groups, where
  $R_3$ represents a hydrogen atom or a $C_{1-4}$-alkyl group,
  a 2-oxomorpholin-4-yl group which may be substituted by 1 or 2 methyl or ethyl groups, or a N-[(1,3-dioxolan-2-yl)methyl]methylamino group, $R_c$ denotes a hydrogen atom, a methoxy, ethoxy, 2-methoxyethoxy, 2-ethoxyethoxy, cyclobutyloxy, cyclopentyloxy, cyclohexyloxy, cyclopropylmethoxy, cyclobutylmethoxy, cyclopentylmethoxy, cyclohexylmethoxy, tetrahydrofuran-3-yloxy, tetrahydropyran-3-yloxy, tetrahydropyran-4-yloxy, tetrahydrofuranylmethoxy, or tetrahydropyranylmethoxy group, and n denotes an integer from the range from 1 to 3 with the proviso that the following compounds:

4-[(3-bromophenyl)amino]-6-({4-[N-(1,3-dioxolan-2-ylmethyl)-N-methylamino]-1-oxo-2-buten-1-yl}amino)-7-methoxyquinazoline;

4-[(3-bromophenyl)amino]-6-{[4-(2-oxomorpholin-4-yl)-1-oxo-2-buten-1-yl]amino}-7-methoxyquinazoline;

4-[(3-bromophenyl)amino]-6-[(4-{N-[(tert-butyloxycarbonyl)methyl]-N-(2-hydroxyethyl)amino}-1-oxo-2-buten-1-yl)amino]-7-methoxyquinazoline;

4-[(3-bromophenyl)amino]-6-({4-[N-(carboxymethyl)-N-(2-hydroxyethyl)amino]-1-oxo-2-buten-1-yl}amino)-7-methoxyquinazoline;

4-[(3-chloro-4-fluorophenyl)amino]-6-{[4-(2-oxomorpholin-4-yl)-1-oxo-2-buten-1-yl]amino}-7-cyclopropylmethoxyquinazoline;

4-[(3-chloro-4-fluorophenyl)amino]-6-[(4-{N-[(ethoxycarbonyl)methyl]-N-(2-hydroxyethyl)amino}-1-oxo-2-buten-1-yl)amino]-7-cyclopropylmethoxyquinazoline;

4-[(3-chloro-4-fluorophenyl)amino]-6-[(4-{N-[(ethoxycarbonyl)methyl]-N-(2-hydroxy-2-methylpropyl)amino}-1-oxo-2-buten-1-yl)amino]-7-cyclopropylmethoxyquinazoline;

4-[(3-chloro-4-fluorophenyl)amino]-6-{[4-(2,2-dimethyl-6-oxomorpholin-4-yl)-1-oxo-2-buten-1-yl]amino}-7-cyclopropylmethoxyquinazoline;

4-[(3-chloro-4-fluorophenyl)amino]-6-{[4-(5,5-dimethyl-2-oxomorpholin-4-yl)-1-oxo-2-buten-1-yl]amino}-7-cyclopropylmethoxyquinazoline;

4-[(3-chloro-4-fluorophenyl)amino]-6-{[4-(5-methyl-2-oxomorpholin-4-yl)-1-oxo-2-buten-1-yl]amino}-7-cyclopropylmethoxyquinazoline;

(R)-4-[(3-chloro-4-fluorophenyl)amino]-6-[(4-{N-[1-(ethoxycarbonyl)ethyl]-N-(2-hydroxyethyl)amino}-1-oxo-2-buten-1-yl)amino]-7-cyclopropylmethoxyquinazoline; and (R)-4-[(3-chloro-4-fluorophenyl)amino]-6-{[4-(3-methyl-2-oxomorpholin-4-yl)-1-oxo-2-buten-1-yl]amino}-7-cyclopropylmethoxyquinazoline are excluded.

Preferred compounds of the above general formula I are those wherein $R_a$ denotes a benzyl or 1-phenylethyl group or a phenyl group substituted by the groups $R_1$ and $R_2$, where
  $R_1$ denotes a hydrogen, fluorine, chlorine, or bromine atom, a methyl, trifluoromethyl, cyano, or ethynyl group, and
  $R_2$ denotes a hydrogen or fluorine atom, $R_b$ denotes an $R_3O$—CO—$CH_2$—N—$CH_2$—$CH_2$—OH group optionally substituted at the methylene groups by 1 or 2 methyl or ethyl groups, where
  $R_3$ represents a hydrogen atom or a $C_{1-4}$-alkyl group,
  a 2-oxomorpholin-4-yl group which may be substituted by 1 or 2 methyl or ethyl groups, or an N-[(1,3-dioxolan-2-yl)methyl]methylamino group, $R_c$ denotes a hydrogen atom, a methoxy, ethoxy, 2-methoxyethoxy, 2-ethoxyethoxy, cyclobutyloxy, cyclopentyloxy, cyclohexyloxy, cyclopropylmethoxy, cyclobutylmethoxy, cyclopentylmethoxy, cyclohexylmethoxy, tetrahydrofuran-3-yloxy, tetrahydropyran-3-yloxy, tetrahydropyran-4-yloxy, tetrahydrofuranylmethoxy, or tetrahydropyranylmethoxy group, and n denotes an integer from the range from 1 to 3 with the proviso that the following compounds:

4-[(3-bromophenyl)amino]-6-({4-[N-(1,3-dioxolan-2-ylmethyl)-N-methylamino]-1-oxo-2-buten-1-yl}amino)-7-methoxyquinazoline;

4-[(3-bromophenyl)amino]-6-{[4-(2-oxomorpholin-4-yl)-1-oxo-2-buten-1-yl]amino}-7-methoxyquinazoline;

4-[(3-bromophenyl)amino]-6-[(4-{N-[(tert-butyloxycarbonyl)methyl]-N-(2-hydroxyethyl)amino}-1-oxo-2-buten-1-yl)amino]-7-methoxyquinazoline;

4-[(3-bromophenyl)amino]-6-({4-[N-(carboxymethyl)-N-(2-hydroxyethyl)amino]-1-oxo-2-buten-1-yl}amino)-7-methoxyquinazoline;

4-[(3-chloro-4-fluorophenyl)amino]-6-{[4-(2-oxomorpholin-4-yl)-1-oxo-2-buten-1-yl]amino}-7-cyclopropylmethoxyquinazoline;

4-[(3-chloro-4-fluorophenyl)amino]-6-[(4-{N-[(ethoxycarbonyl)methyl]-N-(2-hydroxyethyl)amino}-1-oxo-2-buten-1-yl)amino]-7-cyclopropylmethoxyquinazoline;

4-[(3-chloro-4-fluorophenyl)amino]-6-[(4-{N-[(ethoxycarbonyl)methyl]-N-(2-hydroxy-2- methylpropyl)amino}-1-oxo-2-buten-1-yl)amino]-7-cyclopropylmethoxyquinazoline;

4-[(3-chloro-4-fluorophenyl)amino]-6-{[4-(2,2-dimethyl-6-oxomorpholin-4-yl)-1-oxo-2-buten-1-yl]amino}-7-cyclopropylmethoxyquinazoline;

4-[(3-chloro-4-fluorophenyl)amino]-6-{[4-(5,5-dimethyl-2-oxomorpholin-4-yl)-1-oxo-2-buten-1-yl]amino}-7-cyclopropylmethoxyquinazoline;

4-[(3-chloro-4-fluorophenyl)amino]-6-{[4-(5-methyl-2-oxomorpholin-4-yl)-1-oxo-2-buten-1-yl]amino}-7-cyclopropylmethoxyquinazoline;

(R)-4-[(3-chloro-4-fluorophenyl)amino]-6-[(4-{N-[1-(ethoxycarbonyl)ethyl]-N-(2-hydroxyethyl)amino}-1-oxo-2-buten-1-yl)amino]-7-cyclopropylmethoxyquinazoline;

(R)-4-[(3-chloro-4-fluorophenyl)amino]-6-{[4-(3-methyl-2-oxomorpholin-4-yl)-1-oxo-2-buten-1-yl]amino}-7-cyclopropylmethoxyquinazoline;

4-[(3-chloro-4-fluorophenyl)amino]-6-[(4-[N-(1,3-dioxolan-2-ylmethyl)-N-methylamino]-1-oxo-2-buten-1-yl)amino]-7-cyclopropylmethoxyquinazoline;

4-(3-chloro-4-fluorophenyl)amino]-6-{[4-(3-methyl-2-oxomorpholin-4-yl)-1-oxo-2-buten-1-yl]amino}-7-cyclopropylmethoxyquinazoline; and 4-[(3-chloro-4-fluorophenyl)amino]-6-{[4-(6-methyl-2-oxomorpholin-4-yl)-1-oxo-2-buten-1-yl]amino}-7-cyclopropylmethoxyquinazoline, are excluded, the tautomers, the stereoisomers, and the salts thereof.

Particularly preferred compounds of the above general formula I are those wherein $R_a$ denotes a benzyl or 1-phenylethyl group or a phenyl group substituted by the groups $R_1$ and $R_2$, where
$R_1$ denotes a fluorine, chlorine, or bromine atom, or a methyl or ethynyl group, and $R_2$ denotes a hydrogen or fluorine atom, $R_b$ denotes an $R_3O$—CO—$CH_2$—N—$CH_2$—$CH_2$—OH group substituted at the methylene groups by 1 or 2 methyl or ethyl groups, where
$R_3$ represents a $C_{1-4}$-alkyl group,
a 2-oxomorpholin-4-yl group which is substituted by 1 or 2 methyl or ethyl groups, $R_c$ denotes a hydrogen atom, a methoxy, ethoxy, 2-methoxyethoxy, cyclobutyloxy, cyclopentyloxy, cyclopropylmethoxy, cyclobutylmethoxy, tetrahydrofuran-3-yloxy, tetrahydropyran-4-yloxy, tetrahydrofuranylmethoxy, or tetrahydropyranylmethoxy group, and n denotes the number 1 or 2 with the proviso that the following compounds 4-[(3-chloro-4-fluorophenyl)amino]-6-[(4-{N-[(ethoxycarbonyl)methyl]-N-(2-hydroxy-2-methylpropyl)amino}-1-oxo-2-buten-1-yl)amino]-7-cyclopropylmethoxyquinazoline;

4-[(3-chloro-4-fluorophenyl)amino]-6-{[4-(2,2-dimethyl-6-oxomorpholin-4-yl)-1-oxo-2-buten-1-yl]amino}-7-cyclopropylmethoxyquinazoline;

4-[(3-chloro-4-fluorophenyl)amino]-6-{[4-(5,5-dimethyl-2-oxomorpholin-4-yl)-1-oxo-2-buten-1-yl]amino}-7-cyclopropylmethoxyquinazoline;

4-[(3-chloro-4-fluorophenyl)amino]-6-{[4-(5-methyl-2-oxomorpholin-4-yl)-1-oxo-2-buten-1-yl]amino}-7-cyclopropylmethoxyquinazoline;

(R)-4-[(3-chloro-4-fluorophenyl)amino]-6-[(4-{N-[1-(ethoxycarbonyl)ethyl]-N-(2-hydroxyethyl)amino}-1-oxo-2-buten-1-yl)amino]-7-cyclopropylmethoxyquinazoline;

(R)-4-[(3-chloro-4-fluorophenyl)amino]-6-{[4-(3-methyl-2-oxomorpholin-4-yl)-1-oxo-2-buten-1-yl]amino}-7-cyclopropylmethoxyquinazoline;

4-[(3-chloro-4-fluorophenyl)amino]-6-{[4-(3-methyl-2-oxomorpholin-4-yl)-1-oxo-2buten-1-yl]amino}-7-cyclopropylmethoxyquinazoline; and 4-[(3-chloro-4-fluorophenyl)amino]-6-{[4-(6-methyl-2-oxomorpholin-4-yl)-1-oxo-2-buten-1-yl]amino}-7-cyclopropylmethoxyquinazoline are excluded, particularly those wherein $R_a$ denotes a benzyl or 1-phenylethyl group or a phenyl group substituted by the groups $R_1$ and $R_2$, where
$R_1$ denotes a fluorine, chlorine, or bromine atom, and
$R_2$ denotes a hydrogen or fluorine atom, $R_b$ denotes a 2-oxomorpholin-4-yl group which is substituted by 1 or 2 methyl or ethyl groups, $R_c$ denotes a hydrogen atom, or a methoxy, ethoxy, 2-methoxyethoxy, cyclobutyloxy, cyclopentyloxy, cyclopropylmethoxy, tetrahydrofuran-3-yloxy, tetrahydropyran-4-yloxy, tetrahydrofuranylmethoxy, or tetrahydropyranylmethoxy group, and n denotes the number 1, with the proviso that the following compounds 4-[(3-chloro-4-fluorophenyl)amino]-6-{[4-(2,2-dimethyl-6-oxomorpholin-4-yl)-1-oxo-2-buten-1-yl]amino}-7-cyclopropylmethoxyquinazoline;

4-[(3-chloro-4-fluorophenyl)amino]-6-{[4-(5,5-dimethyl-2-oxomorpholin-4-yl)-1-oxo-2-buten-1-yl]amino}-7-cyclopropylmethoxyquinazoline;

4-[(3-chloro-4-fluorophenyl)amino]-6-{[4-(5-methyl-2-oxomorpholin-4-yl)-1-oxo-2-buten-1-yl]amino}-7-cyclopropylmethoxyquinazoline;

(R)-4-[(3-chloro-4-fluorophenyl)amino]-6-{[4-(3-methyl-2-oxomorpholin-4-yl)-1-oxo-2-buten-1-yl]amino}-7-cyclopropylmethoxyquinazoline;

4-[(3-chloro-4-fluorophenyl)amino]-6-{[4-(3-methyl-2-oxomorpholin-4-yl)-1-oxo-2-buten-1-yl]amino}-7-cyclopropylmethoxyquinazoline; and 4-[(3-chloro-4-fluorophenyl)amino]-6-{[4-(6-methyl-2-oxomorpholin-4-yl)-1-oxo-2-buten-1-yl]amino}-7-cyclopropylmethoxyquinazoline, are excluded, the tautomers, the stereoisomers, and the salts thereof.

Most particularly preferred compounds of the above general formula I are those wherein $R_a$ denotes a 1-phenylethyl or a 3-chloro-4-fluorophenyl group, $R_b$ denotes a 2-oxomorpholin-4-yl group which is substituted by 1 or 2 methyl groups, or a 2-oxomorpholin-4-yl group which is substituted by an ethyl group, $R_c$ denotes a hydrogen atom, or a methoxy, 2-methoxyethoxy, cyclobutyloxy, cyclopentyloxy, cyclopropylmethoxy, tetrahydrofuran-3-yloxy, tetrahydropyran-4-yloxy, tetrahydrofuranylmethoxy, or tetrahydropyranylmethoxy group, and n denotes the number 1, with the proviso that the following compounds 4-[(3-chloro-4-fluorophenyl)amino]-6-{[4-(2,2-dimethyl-6-oxomorpholin-4-yl)-1-oxo-2-buten-1-yl]amino}-7-cyclopropylmethoxyquinazoline, 4-[(3-chloro-4-fluorophenyl)amino]-6-{[4-(5,5-dimethyl-2-oxomorpholin-4-yl)-1-oxo-2-buten-1-yl]amino}-7-cyclopropylmethoxyquinazoline, 4-[(3-chloro-4-fluorophenyl)amino]-6-{[4-(5-methyl-2-oxomorpholin-4-yl)-1-oxo-2-buten-1-yl]amino}-7-cyclopropylmethoxyquinazoline, (R)-4-[(3-chloro-4-fluorophenyl)amino]-6-{[4-(3-methyl-2-oxomorpholin-4-yl)-1-oxo-2-buten-1-yl]amino}-7-cyclopropylmethoxyquinazoline, 4-[(3-chloro-4-fluorophenyl)amino]-6-{[4-(3-methyl-2-oxomorpholin-4-yl)-1-oxo-2-buten-1-yl]amino}-7-cyclopropylmethoxyquinazoline, and 4-[(3-chloro-4-fluorophenyl)amino]-6-{[4-(6-methyl-2-oxomorpholin-4-yl)-1-oxo-2-buten-1-yl]amino}-7-cyclopropylmethoxyquinazoline, are excluded, the tautomers, the stereoisomers, and the salts thereof.

The following compounds are mentioned by way of example as being particularly preferred compounds of general formula I:

4-[(3-chloro-4-fluorophenyl)amino]-6-[(4-{N-[(1,3-dioxolan-2-yl)methyl]-N-methylamino}-1-oxo-2-buten-1-yl)amino]-7-cyclopropylmethoxyquinazoline, 4-[(3-chloro-4-fluorophenyl)amino]-6-{[4-((S)-6-methyl-2-oxomorpholin-4-yl)-1-oxo-2-buten-1-yl]amino}-7-cyclopropylmethoxyquinazoline, 4-[(3-chloro-4-fluorophenyl)amino]-6-{[4-((R)-6-methyl-2-oxomorpholin-4-yl)-1-oxo-2-buten-1-yl]amino}-7-cyclopropylmethoxyquinazoline, 4-[(3-chloro-4-fluorophenyl)amino]-6-{[4-((S)-3-methyl-2-oxomorpholin-4-yl)-1-oxo-2-buten-1-yl]amino}-7-cyclopropylmethoxyquinazoline, 4-[(3-chloro-4-fluorophenyl)amino]-6-{[4-(5,5-dimethyl-2-oxomorpholin-4-yl)-1-oxo-2-buten-1-yl]amino}-7-(2-methoxyethoxy)quinazoline, 4-[(3-chloro-4-fluorophenyl)amino]-6-{[4-((S)-6-methyl-2-oxomorpholin-4-yl)-1-oxo-2-buten-1-yl]amino}-7-cyclobutyloxyquinazoline, 4-[(3-chloro-4-fluorophenyl)amino]-6-{[4-((R)-6-methyl-2-oxomorpholin-4-yl)-1-oxo-2-buten-1-yl]amino}-7-cyclobutyloxyquinazoline, 4-[(3-chloro-4-fluorophenyl)amino]-6-{[4-(5,5-dimethyl-2-oxomorpholin-4-yl)-1-oxo-2-buten-1-yl]amino}-7-cyclobutyloxyquinazoline, 4-[(3-chloro-4-fluorophenyl)amino]-6-{[4-(5,5-dimethyl-2-oxomorpholin-4-yl)-1-oxo-2-buten-1-yl]amino}-7-cyclopentyloxyquinazoline, 4-[(R)-(1-phenylethyl)amino]-6-{[4-(5,5-dimethyl-2-oxomorpholin-4-yl)-1-oxo-2-buten-1-yl]amino}quinazoline, 4-[(3-chloro-4-fluorophenyl)amino]-6-{[4-(5,5-dimethyl-2-oxomorpholin-4-yl)-1-oxo-2-buten-1-yl]amino}-7-[(R)-(tetrahydrofuran-3-yl)oxy]quinazoline, 4-[(3-chloro-4-fluorophenyl)amino]-6-{[4-((S)-6-methyl-2-oxomorpholin-4-yl)-1-oxo-2-buten-1-yl]amino}-7-[(S)-(tetrahydrofuran-3-yl)oxy]quinazoline, 4-[(3-chloro-4-fluorophenyl)amino]-6-{[4-((R)-6-methyl-2-oxomorpholin-4-yl)-1-oxo-2-buten-1-yl]amino}-7-[(S)-(tetrahydrofuran-3-yl)oxy]quinazoline, 4-[(3-chloro-4-fluorophenyl)amino]-6-{[4-((R)-6-methyl-2-oxomorpholin-4-yl)-1-oxo-2-buten-1-yl]amino}-7-[(R)-(tetrahydrofuran-3-yl)oxy]quinazoline, 4-[(3-chloro-4-fluorophenyl)amino]-6-{[4-(5,5-dimethyl-2-oxomorpholin-4-yl)-1-oxo-2-buten-1-yl]amino}-7-[(tetrahydropyran-4-yl)oxy]quinazoline, 4-[(R)-(1-phenylethyl)amino]-6-{[4-(5,5-dimethyl-2-oxomorpholin-4-yl)-1-oxo-2buten-1-yl]amino}-7-cyclopropylmethoxyquinazoline, 4-[(3-chloro-4-fluorophenyl)amino]-6-{[4-(2,2-dimethyl-6-oxomorpholin-4-yl)-1-oxo-2-buten-1-yl]amino}-7-[(tetrahydropyran-4-yl)oxy]quinazoline, 4-[(3-chloro-4-fluorophenyl)amino]-6-{[4-(5,5-dimethyl-2-oxomorpholin-4-yl)-1-oxo-2-buten-1-yl]amino}-7-methoxyquinazoline, 4-[(3-chloro-4-fluorophenyl)amino]-6-{[4-(5,5-dimethyl-2-oxomorpholin-4-yl)-1-oxo-2-buten-1-yl]amino}-7-[(tetrahydrofuran-2-yl)methoxy]quinazoline, 4-[(3-chloro-4-fluorophenyl)amino]-6-{[4-(5,5-dimethyl-2-oxomorpholin-4-yl)-1-oxo-2-buten-1-yl]amino}-7-[(S)-(tetrahydrofuran-3-yl)oxy]quinazoline, 4-[(3-chloro-4-fluorophenyl)amino]-6-{[4-(6-ethyl-2-oxomorpholin-4-yl)-1-oxo-2-buten-1-yl]amino}-7-cyclopropylmethoxyquinazoline, 4-[(R)-(1-phenylethyl)amino]-6-{[4-((S)-6-methyl-2-oxomorpholin-4-yl)-1-oxo-2-buten-1-yl]amino}-7-methoxyquinazoline, 4-[(3-chloro-4-fluorophenyl)amino]-6-{[4-((S)-6-methyl-2-oxomorpholin-4-yl)-1-oxo-2-buten-1-yl]amino}-7-[(R)-(tetrahydrofuran-3-yl)oxy]quinazoline, 4-[(3-chloro-4-fluorophenyl)amino]-6-{[4-(5,5-dimethyl-2-oxomorpholin-4-yl)-1-oxo-2-buten-1-yl]amino}quinazoline, 4-[(3-chloro-4-fluorophenyl)amino]-6-{[4-((R)-6-methyl-2-oxomorpholin-4-yl)-1-oxo-2-buten-1-yl]amino}quinazoline, 4-[(3-chloro-4-fluorophenyl)amino]-6-{[4-((R)-6-methyl-2-oxomorpholin-4-yl)-1-oxo-2-buten-1-yl]amino}-7-[(tetrahydropyran-4-yl)oxy]quinazoline, and 4-[(R)-(1-phenylethyl)amino]-6-{[4-((S)-6-methyl-2-oxomorpholin-4-yl)-1-oxo-2-buten-1-yl]amino}quinazoline, the tautomers, the stereoisomers, and the salts thereof.

The compounds of general formula I may be prepared by the following methods, for example:

a) reacting a compound of general formula

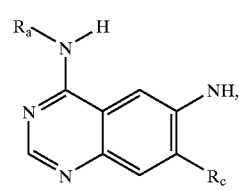

(II)

wherein $R_a$ and $R_c$ are as hereinbefore defined, with a compound of general formula

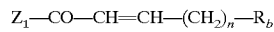

$$Z_1-CO-CH=CH-(CH_2)_n-R_b \quad (III)$$

wherein $R_b$ and n are as hereinbefore defined, and $Z_1$ represents a leaving group such as a halogen atom, e.g., a chlorine or bromine atom, or a hydroxy group.

The reaction is optionally carried out in a solvent or mixture of solvents such as methylene chloride, dimethylformamide, acetonitrile, toluene, chlorobenzene, tetrahydrofuran, methylene chloride/tetrahydrofuran, or dioxane, optionally in the presence of an inorganic or organic base and optionally in the presence of a dehydrating agent, expediently at temperatures between −50° C. and 150° C., preferably at temperatures between −20° C. and 80° C.

With a compound of general formula III wherein $Z_1$ denotes a leaving group, the reaction is optionally carried out in a solvent or mixture of solvents such as methylene chloride, dimethylformamide, acetonitrile, toluene, chlorobenzene, tetrahydrofuran, methylene chloride/tetrahydrofuran, or dioxane conveniently in the presence of a tertiary organic base such as triethylamine, pyridine, or 2-dimethylaminopyridine, or N-ethyldiisopropylamine (Hünig base), while these organic bases may simultaneously also act as solvent, or in the presence of an inorganic base such as sodium carbonate, potassium carbonate, or sodium hydroxide solution expediently at temperatures between −50° C. and 150° C., preferably at temperatures between −20° C. and 80° C.

With a compound of general formula III wherein $Z_1$ denotes a hydroxy group, the reaction is preferably carried out in the presence of a dehydrating agent, e.g., in the presence of isobutyl chloroformate, thionyl chloride, trimethyl chlorosilane, phosphorus trichloride, phosphorus pentoxide, hexamethyldisilazane, N,N'-dicyclohexylcarbodiimide, N,N'-dicyclohexylcarbodiimide/N-hydroxysuccinimide, or 1-hydroxybenzotriazole, and optionally also in the presence of 4-dimethylaminopyridine, N,N'-carbonyldiimidazole, or triphenylphosphine/carbon tetrachloride, expediently in a solvent such as methylene chloride, tetrahydrofuran, dioxane, toluene, chlorobenzene, dimethylsulfoxide, ethylene glycol diethylether, or sulfolane, and optionally in the presence of a reaction accelerator such as 4-dimethylaminopyridine at temperatures between −50° C. and 150° C., but preferably at temperatures between −20° C. and 80° C.

b) reacting a compound of general formula

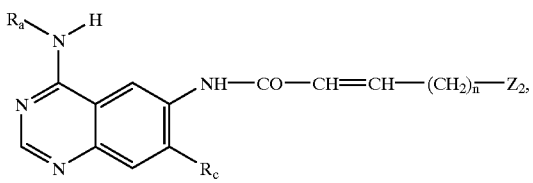

(IV)

optionally formed in the reaction mixture, wherein $R_a$, $R_c$, and n are as hereinbefore defined, and $Z_2$ denotes a leaving group such as a halogen atom or a substituted sulfonyloxy group such as a chlorine or bromine atom, a methanesulfonyloxy or p-toluenesulfonyloxy group, or a hydroxy group, with a compound of general formula H—$R_b$     (V)

wherein $R_b$ is as hereinbefore defined.

The reaction is expediently carried out in a solvent such as isopropanol, acetonitrile, butanol, tetrahydrofuran, dioxane, toluene, chlorobenzene, dimethylformamide, dimethylsulfoxide, methylene chloride, ethylene glycol monomethyl ether, ethylene glycol diethyl ether, or sulfolane, or in a mixture of solvents, optionally in the presence of an inorganic base, e.g., sodium carbonate or potassium hydroxide, or a tertiary organic base, e.g., triethylamine or N-ethyldiisopropylamine (Hünig base), while these organic bases may simultaneously also serve as solvent, and optionally in the presence of a reaction accelerator such as an alkali metal halide at temperatures between −20° C. and 150° C., but preferably at temperatures between −10° C. and 100° C. The reaction may, however, also be carried out without a solvent or in an excess of the compound of general formula V used.

If $Z_2$ in a compound of general formula IV denotes a hydroxy group, the reaction is preferably carried out in the presence of an activating agent, e.g., in the presence of thionyl chloride or phosphorus trichloride, conveniently in a solvent such as acetonitrile, methylene chloride, tetrahydrofuran, dioxane, toluene, chlorobenzene, or ethylene glycol diethyl ether and optionally in the presence of a reaction accelerator such as sodium iodide at temperatures between −50° C. and 150° C., but preferably at temperatures between −20° C. and 80° C.

The compound of formula IV may also be prepared in a one-pot process from the compound of formula II and a corresponding carboxylic acid derivative and further reacted directly.

c) cyclizing a compound of general formula

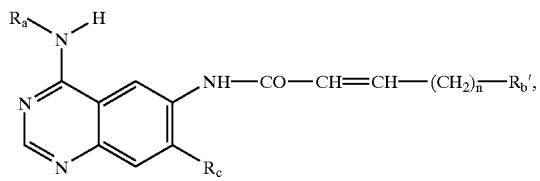

(VI)

optionally formed in the reaction mixture wherein $R_a$, $R_c$, and n are as hereinbefore defined, and $R_b'$ denotes an optionally substituted N-(carboxymethyl)-N-(2-hydroxyethyl)amino or N-($C_{1-4}$-alkyloxycarbonylmethyl)-N-(2-hydroxyethyl)amino group which can be converted by cyclization into an optionally substituted 2-oxomorpholin-4-yl group.

The reaction is optionally carried out in a solvent or mixture of solvents such as methylene chloride, acetonitrile, dimethylformamide, dimethylsulfoxide, sulfolane, benzene, toluene, chlorobenzene, tetrahydrofuran, benzene/tetrahydrofuran, or dioxane, expediently in the presence of an anhydrous acid such as trifluoroacetic acid, methanesulfonic acid, or sulfuric acid or in the presence of a dehydrating agent, e.g., in the presence of isobutyl chloroformate, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, or 1-hydroxybenzotriazole, N,N'-carbonyldiimidazole, or triphenylphosphine/carbon tetrachloride, at temperatures between −20° C. and 200° C., but preferably at temperatures between −10° C. and 160° C.

If according to the invention a compound of general formula I is obtained which contains an optionally substituted 2-oxomorpholin-4-yl group, this may be converted by hydrolysis into a corresponding compound which contains an optionally substituted N-(carboxymethyl)-N-(2-hydroxyethyl)amino group.

The optional subsequent hydrolysis is carried out, for example, by hydrolysis in an aqueous solvent, e.g., in water, isopropanol/water, acetic acid/water, tetrahydrofuran/water, or dioxane/water, in the presence of an acid such as trifluoroacetic acid, hydrochloric acid, or sulfuric acid or in the presence of an alkali metal base such as sodium hydroxide, at temperatures between 0° C. and 120° C., preferably at temperatures between 10° C. and 100° C.

In the reactions described hereinbefore, any reactive groups present such as hydroxy, carboxy, phosphono, or imino groups may be protected during the reaction by conventional protecting groups which are cleaved again after the reaction.

For example, a protecting group for a hydroxy group may be a trimethylsilyl, acetyl, benzoyl, methyl, ethyl, tert-butyl, trityl, benzyl, or tetrahydropyranyl group, protecting groups for a carboxy group may be a trimethylsilyl, methyl, ethyl, tert-butyl, benzyl, or tetrahydropyranyl group, and protecting groups for an imino group may be a formyl, acetyl, trifluoroacetyl, ethoxycarbonyl, tert-butoxycarbonyl, benzyloxycarbonyl, benzyl, methoxybenzyl, or 2,4-dimethoxybenzyl group.

Any protecting group used is optionally subsequently cleaved for example by hydrolysis in an aqueous solvent, e.g., in water, isopropanol/water, acetic acid/water, tetrahydrofuran/water, or dioxane/water, in the presence of an acid such as trifluoroacetic acid, hydrochloric acid, or sulfuric acid, or in the presence of an alkali metal base such as sodium hydroxide or potassium hydroxide or aprotically, e.g., in the presence of iodotrimethylsilane, at temperatures between 0° C. and 120° C., preferably at temperatures between 10° C. and 100° C.

However, a benzyl, methoxybenzyl, or benzyloxycarbonyl group is cleaved, for example hydrogenolytically, e.g., with hydrogen in the presence of a catalyst such as palladium/charcoal in a suitable solvent such as methanol, ethanol, ethyl acetate, or glacial acetic acid, optionally with the addition of an acid such as hydrochloric acid at temperatures between 0° C. and 100° C., but preferably at ambient temperatures between 20° C. and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert-butyl or tert-butyloxycarbonyl group is preferably cleaved by treating with an acid such as trifluoroacetic acid or hydrochloric acid or by treating with iodotrimethylsilane optionally using a solvent such as methylene chloride, dioxane, methanol, or diethyl ether.

A trifluoroacetyl group is preferably cleaved by treating with an acid such as hydrochloric acid, optionally in the presence of a solvent such as acetic acid at temperatures between 50° C. and 120° C. or by treating with sodium hydroxide solution, optionally in the presence of a solvent such as tetrahydrofuran at temperatures between 0° C. and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. N. L. Allinger and E. L. Eliel in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g., by chromatography and/or fractional crystallization, and, if these compounds are obtained in racemic form, they may subsequently be resolved into the enantiomers as mentioned above.

The enantiomers are preferably separated by column separation on chiral phases or by recrystallization from an optically active solvent or by reacting with an optically active substance which forms salts or derivatives such as, e.g., esters or amides with the racemic compound, particularly acids and the activated derivatives or alcohols thereof, and separating the diastereomeric mixture of salts or derivatives thus obtained, e.g., on the basis of their differences in solubility, while the free antipodes may be released from the pure diastereomeric salts or derivatives by the action of suitable agents. Optically active acids in common use are, e.g., the D- and L-forms of tartaric acid or dibenzoyltartaric acid, di-o-tolyltartaric acid, malic acid, mandelic acid, camphorsulfonic acid, glutamic acid, aspartic acid, or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulfuric acid, methanesulfonic acid, phosphoric acid, fumaric acid, succinic acid, lactic acid, citric acid, tartaric acid, or maleic acid.

The compounds of general formulae II to VI used as starting materials are known from the literature in some cases or may be obtained by methods known from the literature (cf. Examples I to VIII).

As already mentioned hereinbefore, the compounds of general formula I according to the invention and the physiologically acceptable salts thereof have valuable pharmacological properties, particularly an inhibiting effect on signal transduction mediated by the Epidermal Growth Factor receptor (EGF-R), while this may be achieved for example by inhibiting ligand bonding, receptor dimerization, or tyrosine kinase itself. It is also possible that the transmission of signals to components located further down is blocked.

The biological properties of the new compounds were investigated as follows:

The inhibition of the EGF-R-mediated signal transmission can be demonstrated, e.g., with cells which express human EGF-R and whose survival and proliferation depend on stimulation by EGF or TGF-alpha. A cell line of murine origin dependent on interleukin-3-(IL-3) which was genetically modified to express functional human EGF-R was used here. The proliferation of these cells known as F/L-HERc can therefore be stimulated either by murine IL-3 or by EGF (cf. T. von Rüden et al. in EMBO J. 7, 2749–2756 (1988) and J. H. Pierce et al. in Science 239, 628–631 (1988)).

The starting material used for the F/L-HERc cells was the cell line FDC-$P_1$, the production of which has been described by T. M. Dexter et al. in J. Exp. Med. 152, 1036–1047 (1980). Alternatively, however, other growth-factor-dependent cells may also be used (cf., for example, J. H. Pierce et al. in Science 239, 628–631 (1988), H. Shibuya et al. in Cell 70, 57–67 (1992) and W. S. Alexander et al. in EMBO J. 10, 3683–3691 (1991)). For expressing the human EGF-R cDNA (cf. A. Ullrich et al. in Nature 309, 418–425 (1984)) recombinant retroviruses were used as described by T. von Rüden et al., EMBO J. 7, 2749–2756 (1988), except that the retroviral vector LXSN (cf. A. D. Miller et al. in BioTechniques 7, 980–990 (1989)) was used for the expression of the EGF-R cDNA and the line GP+E86 (cf. D. Markowitz et al. in J. Virol. 62, 1120–1124 (1988)) was used as the packaging cell.

The test was performed as follows:

F/L-HERc cells were cultivated in RPMI/1640 medium (Bio Whittaker), supplemented with 10% fetal calf serum (FCS, Boehringer Mannheim), 2 mM glutamine (Bio Whittaker), standard antibiotics and 20 ng/ml of human EGF (Promega), at 37° C. and 5% $CO_2$. In order to investigate the inhibitory activity of the compounds according to the invention, $1.5 \times 10^4$ cells per well were cultivated in triplicate in 96-well dishes in the above medium (200 µl), the cell proliferation being stimulated with either EGF (20 ng/ml) or murine IL-3. The IL-3 used was obtained from culture supernatants of the cell line X63/0 mIL-3 (cf. H. Karasuyama et al. in Eur. J. Immunol. 18, 97–104 (1988)). The compounds according to the invention were dissolved in 100% dimethylsulfoxide (DMSO) and added to the cultures in various dilutions, the maximum DMSO concentration being 1%. The cultures were incubated for 48 hours at 37° C.

In order to determine the inhibitory activity of the compounds according to the invention the relative cell number was measured in O.D. units using the Cell Titer 96™ Aqueous Non-Radioactive Cell Proliferation Assay (Promega). The relative cell number was calculated as a percentage of the control (F/LHERc cells without inhibitor) and the concentration of active substance which inhibits the proliferation of the cells by 50% ($IC_{50}$) was derived therefrom. The following results were obtained:

| Compound (Example No.) | Inhibition of EGF-Dependent Proliferation $IC_{50}$ [nM] |
| --- | --- |
| 2 | 15 |
| 2(1) | 9 |
| 1(2) | 0.02 |

The compounds of general formula I according to the invention thus inhibit signal transduction by tyrosine kinases, as demonstrated by the example of the human EGF receptor, and are therefore useful for treating pathophysiological processes caused by hyperfunction of tyrosine kinases. These are, e.g., benign or malignant tumors, particularly tumors of epithelial and neuroepithelial origin, metastasization, and the abnormal proliferation of vascular endothelial cells (neoangiogenesis).

The compounds according to the invention are also useful for preventing and treating diseases of the airways and lungs which are accompanied by increased or altered production of mucus caused by stimulation by tyrosine kinases, e.g., in inflammatory diseases of the airways such as chronic bronchitis, chronic obstructive bronchitis, asthma, bronchiectasis, allergic or non-allergic rhinitis or sinusitis, cystic fibrosis, α1-antitrypsin deficiency, or coughs, pulmonary emphysema, pulmonary fibrosis, and hyperreactive airways.

The compounds are also suitable for treating diseases of the gastrointestinal tract and bile duct and gall bladder which are associated with disrupted activity of the tyrosine kinases, such as may be found, e.g., in chronic inflammatory changes such as cholecystitis, Crohn's disease, ulcerative colitis, and ulcers in the gastrointestinal tract or such as may occur in diseases of the gastrointestinal tract which are associated with increased secretions, such as Ménétrier's disease, secreting adenomas, and protein loss syndrome, and also for treating nasal polyps and polyps of the gastrointestinal tract of various origins such as villous or adenomatous polyps of the large intestine, but also polyps in familial polyposis coli, in intestinal polyps in Gardner's syndrome, in polyps throughout the entire gastrointestinal tract in Peutz-Jeghers Syndrome, in inflammatory pseudopolyps, in juvenile polyps, in colitis cystica profunda and in pneumatosis cystoides intestinales.

In addition, the compounds of general formula I and the physiologically acceptable salts thereof may be used to treat kidney diseases, particularly in cystic changes as in cystic kidneys, for treating renal cysts which may be idiopathic in origin or occur in syndromes such as tubercular sclerosis, in von Hippel-Lindau syndrome, in nephrophthisis, and spongy kidney and other diseases caused by abnormal function of tyrosine kinases, such as, e.g., epidermal hyperproliferation (psoriasis), inflammatory processes, diseases of the immune system, hyperproliferation of hematopoietic cells, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g., etoposide), mitosis inhibitors (e.g., vinblastine), compounds which interact with nucleic acids (e.g., cis-platin, cyclophosphamide, adriamycin), hormone antagonists (e.g., tamoxifen), inhibitors of metabolic processes (e.g., 5-FU etc.), cytokines (e.g., interferons), antibodies, etc. For treating respiratory tract diseases, these compounds may be used on their own or in conjunction with other therapeutic agents for the airways, such as substances with a secretolytic, broncholytic, and/or anti-inflammatory activity. For treating diseases in the region of the gastrointestinal tract, these compounds may also be administered on their own or in conjunction with substances having an effect on motility or secretion, or anti-inflammatory substances. These combinations may be administered either simultaneously or sequentially.

These compounds may be administered either on their own or in conjunction with other active substances by intravenous, subcutaneous, intramuscular, intraperitoneal, or intranasal route, by inhalation or transdermally or orally, while aerosol formulations are particularly suitable for inhalation.

For pharmaceutical use the compounds according to the invention are generally used for warm-blooded vertebrates, particularly humans, in doses of 0.01–100 mg/kg of body weight, preferably 0.1–15 mg/kg. For administration they are formulated with one or more conventional inert carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose, or fatty substances such as hard fat or suitable mixtures thereof in conventional galenic preparations such as plain or coated tablets, capsules, powders, suspensions, solutions, sprays, or suppositories.

The following Examples are intended to illustrate the present invention without restricting it:

Preparation of the starting compounds:

EXAMPLE I

6-Amino-4-[(3-chloro-4-fluorophenyl)amino]-7-cyclopropylmethoxyquinazoline 36.02 g of 4-[(3-chloro-4-fluorophenyl)amino]-7-cyclopropylmethoxy-6-nitroquinazoline are suspended in a mixture of 1080 ml of ethanol, 144 ml of glacial acetic acid, and 360 ml of water and refluxed, during which time the substance goes into solution. 20.70 g of iron powder are then carefully added in batches. After 30 minutes, the reaction is complete and the reaction mixture is evaporated to dryness. The residue is taken up in 1200 ml of methylene chloride/methanol (9:1) and made alkaline with 33% ammonia solution. The iron slurry is suction filtered through and washed with 500 ml of methylene chloride/methanol (9:1). The brown filtrate is filtered through a silica gel packing, washed with a total of 2000 ml of methylene chloride/methanol (9:1), and concentrated by evaporation. The flask residue is suspended with 140 ml of diethylether, suction filtered, and air dried. Yield: 29.70 g (89% of theory); melting point: 208° C.; mass spectrum (ESI$^+$): m/z=359, 361 [M+H]$^+$.

The following compounds are obtained analogously to Example I:

(1) 6-Amino-4-[(3-chloro-4-fluorophenyl)amino]-7-(2-methoxyethoxy)quinazoline $R_f$ value: 0.48 (silica gel, ethyl acetate/methanol=9:1); mass spectrum (ESI$^+$): m/z=363, 365 [M+H]$^+$.

(2) 6-Amino-4-[(3-chloro-4-fluorophenyl)amino]-7-cyclobutyloxyquinazoline

Melting point: 238° C.; mass spectrum (ESI$^+$): m/z=359, 361 [M+H]$^+$.

(3) 6-Amino-4-[(3-chloro-4-fluorophenyl)amino]-7-cyclopentyloxyquinazoline

Melting point: 204° C.; mass spectrum (ESI$^+$): m/z=373, 375 [M+H]$^+$.

(4) 6-Amino-4-[(R)-(1-phenylethyl)amino]quinazoline $R_f$ value: 0.12 (silica gel, ethyl acetate); mass spectrum (EI): m/z=264 [M]$^+$.

(5) 6-Amino-4-[(3-chloro-4-fluorophenyl)amino]-7-[(R)-(tetrahydrofuran-3-yl)oxy]quinazoline $R_f$ value: 0.27 (silica gel, ethyl acetate/methanol=9:1); mass spectrum (ESI$^+$): m/z=375, 377 [M+H]$^+$.

(6) 6-Amino-4-[(3-chloro-4-fluorophenyl)amino]-7-[(S)-(tetrahydrofuran-3-yl)oxy]quinazoline $R_f$ value: 0.27 (silica gel, ethyl acetate/methanol=9:1); mass spectrum (ESI$^-$): m/z=373, 375 [M−H]$^-$.

(7) 6-Amino-4-[(3-chloro-4-fluorophenyl)amino]-7-[(tetrahydropyran-4-yl)oxy]quinazoline $R_f$ value: 0.41 (silica gel, ethyl acetate/methanol=9:1); mass spectrum (ESI$^-$): m/z=387, 389 [M−H]$^-$.

(8) 6-Amino-4-[(R)-(1-phenylethyl)amino]-7-cyclopropylmethoxyquinazoline $R_f$ value: 0.54 (silica gel, ethyl acetate); mass spectrum (ESI$^+$): m/z=335 [M+H]$^+$.

(9) 6-Amino-4-[(3-chloro-4-fluorophenyl)amino]-7-[(tetrahydrofuran-2-yl)methoxy]quinazoline Melting point value: 162° C.–164° C.; mass spectrum (ESI$^-$): m/z=387, 389 [M−H]$^-$.

(10) 6-Amino-4-[(R)-(1-phenylethyl)amino]-7-methoxyquinazoline $R_f$ value: 0.42 (silica gel, methylene chloride/methanol/concentrated aqueous ammonia solution=90:10:1); mass spectrum (ESI$^+$): m/z=295 [M+H]$^+$.

(11) 6-Amino-4-[(3-chloro-4-fluorophenyl)amino]-7-[(tetrahydrofuran-3-yl)methoxy]quinazoline $R_f$ value: 0.40 (silica gel, ethyl acetate/methanol=9:1); mass spectrum (ESI$^-$): m/z=387, 389 [M−H]$^-$.

(12) 6-Amino-4-[(3-chloro-4-fluorophenyl)amino]-7-[(tetrahydropyran-4-yl)methoxy]quinazoline $R_f$ value: 0.41 (silica gel, ethyl acetate/methanol=9:1); mass spectrum (ESI$^+$): m/z=403, 405 [M+H]$^+$.

EXAMPLE II

4-[(3-chloro-4-fluorophenyl)amino]-7-cyclopropylmethoxy-6-nitroquinazoline 29.36 g of cyclopropylmethanol are dissolved in 310 ml of N,N-dimethylformamide and cooled to about 10° C. in an ice bath. Then 41.58 g potassium tert-butoxide is added in batches, while the temperature should stay below 15° C. The reaction mixture is then stirred for another 30 minutes at 10° C., then 31.19 g of 4-[(3-chloro-4-fluorophenyl)amino]-7-fluoro-6-nitroquinazoline is added in batches, while again the temperature should not exceed 15° C. The dark red reaction mixture is stirred for another hour at 15° C. For working up, the mixture is poured onto 2.5 l of water and neutralized with 2N hydrochloric acid. The yellowish precipitate formed is suction filtered, washed with water, and dried at 50° C. in a drying cupboard. Yield: 36.02 g (100% of theory); melting point: 204° C.; mass spectrum (ESI$^+$): m/z=389, 391 [M+H]$^+$.

The following compounds are obtained analogously to Example II:

(1) 4-[(3-chloro-4-fluorophenyl)amino]-7-(2-methoxyethoxy)-6-nitroquinazoline

Melting point: 208° C.; mass spectrum (ESI$^+$): m/z=393, 395 [M+H]$^+$.

(2) 4-[(3-chloro-4-fluorophenyl)amino]-7-cyclobutyloxy-6-nitroquinazoline

Melting point: 235° C.; mass spectrum (ESI$^+$): m/z=389, 391 [M+H]$^+$.

(3) 4-[(3-chloro-4-fluorophenyl)amino]-7-cyclopentyloxy-6-nitroquinazoline

Melting point: 230° C.; mass spectrum (ESI$^+$): m/z=403, 405 [M+H]$^+$.

(4) 4-[(3-chloro-4-fluorophenyl)amino]-6-nitro-7-[(R)-(tetrahydrofuran-3-yl)oxy]quinazoline Melting point: 244° C.; mass spectrum (ESI$^+$): m/z=405, 407 [M+H]$^+$.

(5) 4-[(3-chloro-4-fluorophenyl)amino]-6-nitro-7-[(S)-(tetrahydrofuran-3-yl)oxy]quinazoline $R_f$ value: 0.45 (silica gel, ethyl acetate); mass spectrum (ESI$^+$): m/z=405, 407 [M+H]$^+$.

(6) 4-[(3-chloro-4-fluorophenyl)amino]-6-nitro-7-[(tetrahydropyran-4-yl)oxy]quinazoline $R_f$ value: 0.41 (silica gel, ethyl acetate); mass spectrum (ESI$^-$): m/z=417, 419 [M−H]$^-$.

(7) 4-[(R)-(1-phenylethyl)amino]-7-cyclopropylmethoxy-6-nitroquinazoline $R_f$ value: 0.24 (silica gel, cyclohexane/ethyl acetate=1:1); mass spectrum (ESI$^-$): m/z=363 [M−H]$^-$.

(8) 4-[(3-chloro-4-fluorophenyl)amino]-6-nitro-7-[(tetrahydrofuran-2-yl)methoxy]quinazoline $R_f$ value: 0.47 (silica gel, ethyl acetate); mass spectrum (ESI$^-$): m/z=417, 419 [M−H]$^-$.

(9) 4-[(R)-(1-phenylethyl)amino]-7-methoxy-6-nitroquinazoline

The reaction is carried out with sodium methoxide in tetrahydrofuran. $R_f$ value: 0.17 (silica gel, cyclohexane/ethyl acetate=1:1); mass spectrum (ESI$^-$): m/z=323 [M−H]$^-$.

(10) 4-[(3-chloro-4-fluorophenyl)amino]-6-nitro-7-[(tetrahydrofuran-3-yl)methoxy]quinazoline $R_f$ value: 0.41 (silica gel, ethyl acetate); mass spectrum (ESI$^-$): m/z=417, 419 [M−H]$^-$.

(11) 4-[(3-chloro-4-fluorophenyl)amino]-6-nitro-7-[(tetrahydropyran-4-yl)methoxy]quinazoline The reaction is carried out with sodium hydride in tetrahydrofuran. $R_f$ value: 0.78 (silica gel, ethyl acetate/methanol=9:1); mass spectrum (ESI$^-$): m/z=431, 433 [M−H]$^-$.

EXAMPLE III tert-butyl(S)-(2-hydroxypropylamino)acetate 5.91 ml of tert-butyl bromoacetate is added dropwise within 30 minutes to a mixture of 15.00 g of (S)-(+)-1-amino-2-propanol and 6.97 ml of diisopropylethylamine in 100 ml of N,N-dimethylformamide, while cooling with an ice bath. Then the cooling bath is removed and the reaction mixture is stirred overnight at ambient temperature. For working up, the solvent is distilled off in vacuo, the flask residue is dissolved in 50 ml water and saturated with 15 g of sodium chloride. The aqueous phase is extracted several times with ethyl acetate. The extracts are combined, washed with 20 ml of saturated sodium chloride solution, dried over magnesium sulfate, and concentrated by evaporation. The oily yellowish crude product is reacted further without any more purification. Yield: 7.80 g (103% of theory); $R_f$ value: 0.42 (silica gel, methylene chloride/methanol=9:1); mass spectrum (ESI$^+$): m/z=190 [M+H]$^+$.

The following compounds are obtained analogously to Example III:

(1) tert-butyl (R)-(2-hydroxypropylamino)acetate $R_f$ value: 0.42 (silica gel, methylene chloride/methanol=9:1); mass spectrum (ESI$^+$): m/z=190 [M+H]$^+$.

(2) tert-butyl (2-hydroxy-1,1-dimethylethylamino)acetate $R_f$ value: 0.67 (silica gel, ethyl acetate/methanol=9:1); mass spectrum (ESI$^+$): m/z=204 [M+H]$^+$.

EXAMPLE IV

4-[(R)-(1-phenylethyl)amino]-6-nitroquinazoline

A mixture of 6.40 ml of (R)-(1-phenylethyl)amine and 8.70 ml of diisopropylethylamine in 30 ml methylene chloride is added dropwise to 9.00 g of 4-chloro-6-nitroquinazoline in 70 ml methylene chloride while cooling with an ice bath. The mixture is allowed to come up to ambient temperature, then it is stirred for about another 48 hours. For working up, the reaction mixture is washed with water, 10% citric acid, and again with water. The organic phase is dried over magnesium sulfate and concentrated by evaporation. The solid evaporation residue is stirred with about 100 ml methanol, suction filtered, and washed with a little methanol. Yield: 8.44 g (67% of theory); $R_f$ value: 0.33 (silica gel, cyclohexane/ethyl acetate=1:1); mass spectrum (ESI$^-$): m/z=293 [M–H]$^-$.

The following compound is obtained analogously to Example IV:

(1) 4-[(R)-(1-phenylethyl)amino]-7-fluoro-6-nitroquinazoline $R_f$ value: 0.52 (silica gel, cyclohexane/ethyl acetate=1:1); mass spectrum (ESI$^-$): m/z=311 [M–H]$^-$.

EXAMPLE V

Ethyl(2-hydroxy-2-methylpropylamino)acetate 100.00 g of sodium carbonate is added to 50.00 g of glycine ethyl ester hydrochloride in 100 ml of saturated potassium carbonate solution while cooling. The resulting mass is extracted several times with a total of about 600 ml of diethyl ether. The combined ether extracts are dried over sodium sulfate and evaporated to dryness. 28.60 g of glycine ethyl ester are left.

This is mixed with 26.00 ml of isobutylene oxide and 40 ml of absolute ethanol and heated to 90° C. for 6 hours in a Roth bomb. After cooling to ambient temperature, the reaction mixture is evaporated to dryness, leaving a runny oil. Yield: 45.80 g (73% of theory); mass spectrum (ESI$^+$): m/z=176 [M+H]$^+$.

The following compound is obtained analogously to Example V:

(1) [N-benzyl-N-(2-hydroxybutyl)amino]acetic acid

Obtained by reacting benzylglycine with 1,2-epoxybutane in 1N sodium hydroxide solution.

Mass spectrum (ESI$^-$): m/z=236 [M–H]$^-$.

EXAMPLE VI

Methyl(2-hydroxybutylamino)acetate hydrochloride 2.85 g of (2-hydroxybutylamino)acetic acid in 100 ml of methanol are cooled in an ice-acetone cooling bath, then 7.27 ml of thionyl chloride is added dropwise within 20 minutes. The reaction mixture is left overnight to come back to ambient temperature and then evaporated to dryness. Methanol is added several times to the residue and this is then concentrated by evaporation. The crude product is reacted further without any more purification. Yield: 3.83 g (100% of theory); $R_f$ value: 0.85 (reversed phase ready-made TLC plate (E. Merck), methanol/5% sodium chloride solution=6:4); mass spectrum (ESI$^+$): m/z=162 [M+H]$^+$.

EXAMPLE VII (2-hydroxybutylamino)acetic acid 4.60 g of [N-benzyl-N-(2-hydroxybutyl)amino]acetic acid are dissolved in a mixture of methanol and water (7:1) and hydrogenated in the presence of palladium (10% on activated charcoal) as catalyst for about 2.5 hours at ambient temperature until the calculated amount of hydrogen has been taken up. For working up, the catalyst is filtered off and the filtrate evaporated down in vacuo, leaving a white solid. Yield: 2.77 g (97% of theory); $R_f$ value: 0.86 (Reversed phase ready-made TLC plate (E. Merck), acetonitrile/water/trifluoroacetic acid=50:50:1); mass spectrum (ESI$^-$): m/z=146 [M–H]$^-$.

EXAMPLE VIII

Ethyl(2-hydroxy-1,1-dimethylethylamino)acetate hydrochloride 63.00 g of tert-butyl(2-hydroxy-1,1-dimethylethylamino)acetate are placed in 500 ml of ethanol. Then, while cooling with an ice bath, about 200 g of hydrogen chloride are introduced over a period of about four hours. The reaction mixture is stirred overnight at ambient temperature. For working up, it is concentrated by evaporation and stirred with toluene. Then the toluene is distilled off. A viscous oil remains, which is reacted further without any additional purification. $R_f$ value: 0.16 (silica gel, ethyl acetate/methanol=9:1); mass spectrum (ESI$^+$): m/z=176 [M+H]$^+$.

Preparation of the final compounds:

EXAMPLE 1

4-[(3-chloro-4-fluorophenyl)amino]-6-[(4-{N-[(tert-butyloxycarbonyl)methyl]-N-((S)-2-hydroxyprop-1-yl)amino}-1-oxo-2-buten-1-yl)amino]-7-cyclopropylmethoxyquinazoline 0.67 ml of oxalyl chloride is pipetted into 644 mg of bromocrotonic acid in 15 ml methylene chloride, then one drop of N,N-dimethylformamide is added. The reaction mixture is stirred for about an hour at ambient temperature until the development of gas has ended and then evaporated to dryness. The crude bromocrotonic acid chloride is taken up in 10 ml of methylene chloride and, while cooling with an ice bath, added dropwise within five minutes to a solution of 1.00 g of 6-amino-4-[(3-chloro-4-fluorophenyl)amino]-7-cyclopropylmethoxyquinazoline and 2.5 ml of diisopropylethylamine in 30 ml of tetrahydrofuran. The reaction mixture is stirred for one hour while cooling with an ice bath, then for two hours at ambient temperature. 2.64 g of tert-butyl(S)-(2-hydroxypropylamino)acetate, dissolved in 5 ml methylene chloride, are then added. The reaction mixture is stirred overnight at ambient temperature and then for a further five hours at 60° C. For working up, it is evaporated to dryness. The flask residue is taken up in ethyl acetate, washed with 5% citric acid, water, and saturated sodium chloride solution, dried over magnesium sulfate, and concentrated by evaporation. The crude product is purified by chromatography over a silica gel column with ethyl acetate as eluant. Yield: 1.10 g (64% of theory); $R_f$ value: 0.54 (silica gel, methylene chloride/methanol=9:1); mass spectrum (ESI$^-$): m/z=612, 614 [M–H]$^-$.

The following compounds are obtained analogously to Example 1:

(1) 4-[(3-chloro-4-fluorophenyl)amino]-6-[(4-{N-[(tert-butyloxycarbonyl)methyl]-N-((R)-2-hydroxyprop-1-yl)amino}-1-oxo-2-buten-1-yl)amino]-7-cyclopropylmethoxyquinazoline.

$R_f$ value: 0.54 (silica gel, methylene chloride/methanol=9:1); mass spectrum (ESI$^-$): m/z=612, 614 [M–H]$^-$.

(2) 4-[(3-chloro-4-fluorophenyl)amino]-6-[(4-{N-[(1,3-dioxolan-2-yl)methyl]-N-methylamino}-1-oxo-2-buten-1-yl)amino]-7-cyclopropylmethoxyquinazoline.

Melting point: 121° C.; mass spectrum (EI): m/z=541, 543 [M]$^+$.

(3) 4-[(3-chloro-4-fluorophenyl)amino]-6-[(4-{N-[(S)-1-(ethoxycarbonyl)ethyl]-N-(2-hydroxyethyl)amino}-1-oxo-2-buten-1-yl)amino]-7-cyclopropylmethoxyquinazoline.

The starting material ethyl(S)-2-(2-hydroxyethylamino) propionate is obtained by reacting ethyl(R)-2-(trifluoromethylsulfonyloxy)propionate with 2-aminoethanol in methylene chloride. Mass spectrum (EI): m/z=585, 587 [M]$^+$.

(4) 4-[(3-chloro-4-fluorophenyl)amino]-6-{[4-(5,5-dimethyl-2-oxomorpholin-4-yl)-1-oxo-2-buten-1-yl]amino}-7-(2-methoxyethoxy)quinazoline.

Ethyl(2-hydroxy-1,1-dimethylethylamino)acetate hydrochloride is used as starting material.

The cyclized product is obtained. $R_f$ value: 0.40 (silica gel, ethyl acetate/methanol=9:1); mass spectrum (ESI$^+$): m/z=558, 560 [M+H]$^+$.

(5) 4-[(3-chloro-4-fluorophenyl)amino]-6-[(4-{N-[(tert-butyloxycarbonyl)methyl]-N-((S)-2-hydroxyprop-1-yl)amino}-1-oxo-2-buten-1-yl)amino]-7-cyclobutyloxyquinazoline.

$R_f$ value: 0.52 (silica gel, methylene chloride/methanol=95:5); mass spectrum (ESI$^-$): m/z=612, 614 [M–H]$^-$.

(6) 4-[(3-chloro-4-fluorophenyl)amino]-6-[(4-{N-[(tert-butyloxycarbonyl)methyl]-N-((R)-2-hydroxyprop-1-yl)amino}-1-oxo-2-buten-1-yl)amino]-7-cyclobutyloxyquinazoline.

$R_f$ value: 0.52 (silica gel, methylene chloride/methanol=95:5); mass spectrum (ESI$^-$): m/z=612, 614 [M–H]$^-$.

(7) 4-[(3-chloro-4-fluorophenyl)amino]-6-{[4-(5,5-dimethyl-2-oxomorpholin-4-yl)-1-oxo-2-buten-1-yl]amino}-7-cyclobutyloxyquinazoline.

Ethyl(2-hydroxy-1,1-dimethylethylamino)acetate hydrochloride is used as starting material.

The cyclized product is obtained. $R_f$ value: 0.42 (silica gel, methylene chloride/methanol=9:1); mass spectrum (ESI$^+$): m/z=554, 556 [M+H]$^+$.

(8) 4-[(3-chloro-4-fluorophenyl)amino]-6-{[4-(5,5-dimethyl-2-oxomorpholin-4-yl)-1-oxo-2-buten-1-yl]amino}-7-cyclopentyloxyquinazoline.

Ethyl(2-hydroxy-1,1-dimethylethylamino)acetate hydrochloride is used as starting material.

The cyclized product is obtained. $R_f$ value: 0.42 (silica gel, methylene chloride/methanol=9:1); mass spectrum (ESI$^+$): m/z=568, 570 [M+H]$^+$.

(9) 4-[(R)-(1-phenylethyl)amino]-6-{[4-(5,5-dimethyl-2-oxomorpholin-4-yl)-1-oxo-2-buten-1-yl]amino}quinazoline.

Ethyl(2-hydroxy-1,1-dimethylethylamino)acetate hydrochloride is used as starting material.

The cyclized product is obtained. $R_f$ value: 0.48 (silica gel, ethyl acetate/methanol=9:1); mass spectrum (ESI$^-$): m/z=485 [M–H]$^-$.

(10) 4-[(3-chloro-4-fluorophenyl)amino]-6-{[4-(5,5-dimethyl-2-oxomorpholin-4-yl)-1-oxo-2-buten-1-yl]amino}-7-[(R)-(tetrahydrofuran-3-yl)oxy]quinazoline.

Ethyl(2-hydroxy-1,1-dimethylethylamino)acetate hydrochloride is used as starting material.

The cyclized product is obtained. $R_f$ value: 0.36 (silica gel, ethyl acetate/methanol=9:1); mass spectrum (ESI$^-$): m/z=568, 570 [M–H]$^-$.

(11) 4-[(3-chloro-4-fluorophenyl)amino]-6-[(4-{N-[(tert-butyloxycarbonyl)methyl]-N-((S)-2-hydroxyprop-1-yl)amino}-1-oxo-2-buten-1-yl)amino]-7-[(S)-(tetrahydrofuran-3-yl)oxy]quinazoline.

$R_f$ value: 0.44 (silica gel, methylene chloride/methanol=95:5); mass spectrum (ESI$^-$): m/z=628, 630 [M–H]$^-$.

(12) 4-[(3-chloro-4-fluorophenyl)amino]-6-[(4-{N-[(tert-butyloxycarbonyl)methyl]-N-((R)-2-hydroxyprop-1-yl)amino}-1-oxo-2-buten-1-yl)amino]-7-[(S)-(tetrahydrofuran-3-yl)oxy]quinazoline.

$R_f$ value: 0.40 (silica gel, methylene chloride/methanol=95:5); mass spectrum (ESI$^-$): m/z=628, 630 [M–H]$^-$.

(13) 4-[(3-chloro-4-fluorophenyl)amino]-6-[(4-{N-[(tert-butyloxycarbonyl)methyl]-N-((R)-2-hydroxyprop-1-yl)amino}-1-oxo-2-buten-1-yl)amino]-7-[(R)-(tetrahydrofuran-3-yl)oxy]quinazoline.

$R_f$ value: 0.40 (silica gel, methylene chloride/methanol=95:5); mass spectrum (ESI$^-$): m/z=628, 630 [M–H]$^-$.

(14) 4-[(3-chloro-4-fluorophenyl)amino]-6-{[4-(5,5-dimethyl-2-oxomorpholin-4-yl)-1-oxo-2-buten-1-yl]amino}-7-[(tetrahydropyran-4-yl)oxy]quinazoline.

Ethyl(2-hydroxy-1,1-dimethylethylamino)acetate hydrochloride is used as starting material.

The cyclized product is obtained). $R_f$ value: 0.54 (silica gel, ethyl acetate/methanol=9:1); mass spectrum (ESI$^-$): m/z=582, 584 [M–H]$^-$.

(15) 4-[(R)-(1-phenylethyl)amino]-6-{[4-(5,5-dimethyl-2-oxomorpholin-4-yl)-1-oxo-2-buten-1-yl]amino}-7-cyclopropylmethoxyquinazoline.

Ethyl(2-hydroxy-1,1-dimethylethylamino)acetate hydrochloride is used as starting material.

The cyclized product is obtained. $R_f$ value: 0.31 (silica gel, methylene chloride/methanol=95:5); mass spectrum (ESI$^-$): m/z=528 [M–H]$^-$.

(16) 4-[(3-chloro-4-fluorophenyl)amino]-6-[(4-{N-[(ethoxycarbonyl)methyl]-N-(2-hydroxy-2-methylprop-1-yl)amino}-1-oxo-2-buten-1-yl)amino]-7-[(tetrahydropyran-4-yl)oxy]quinazoline.

$R_f$ value: 0.28 (silica gel, methylene chloride/methanol=95:5)

(17) 4-[(3-chloro-4-fluorophenyl)amino]-6-{[4-(5,5-dimethyl-2-oxomorpholin-4-yl)-1-oxo-2-buten-1-yl]amino}-7-methoxyquinazoline.

Ethyl(2-hydroxy-1,1-dimethylethylamino)acetate hydrochloride is used as starting material.

The cyclized product is obtained. $R_f$ value: 0.30 (silica gel, methylene chloride/methanol=15:1); mass spectrum (ESI$^+$): m/z=514, 516 [M+H]$^+$.

(18) 4-[(3-chloro-4-fluorophenyl)amino]-6-{[4-(5,5-dimethyl-2-oxomorpholin-4-yl)-1-oxo-2-buten-1-yl]amino}-7-[(tetrahydrofuran-2-yl)methoxy]quinazoline.

Ethyl(2-hydroxy-1,1-dimethylethylamino)acetate hydrochloride is used as starting material.

The cyclized product is obtained. $R_f$ value: 0.32 (silica gel, methylene chloride/methanol=15:1); mass spectrum (EI): m/z=583, 585 [M]$^+$.

(19) 4-[(3-chloro-4-fluorophenyl)amino]-6-{[4-(5,5-dimethyl-2-oxomorpholin-4-yl)-1oxo-2-buten-1-yl]amino}-7-[(S)-(tetrahydrofuran-3-yl)oxy]quinazoline.

Ethyl(2-hydroxy-1,1-dimethylethylamino)acetate hydrochloride is used as starting material.

The cyclized product is obtained. $R_f$ value: 0.32 (silica gel, methylene chloride/methanol=15:1); mass spectrum (ESI$^-$): m/z=568, 570 [M−H]$^-$.

(20) 4-[(3-chloro-4-fluorophenyl)amino]-6-{[4-(6-ethyl-2-oxomorpholin-4-yl)-1-oxo-2-buten-1-yl]amino}-7-cyclopropylmethoxyquinazoline.

A mixture of cyclized and open-ring product is obtained which is converted into the cyclized product by subsequent treatment with methanesulfonic acid. $R_f$ value: 0.65 (silica gel, methylene chloride/methanol=15:1); mass spectrum (ESI$^-$): m/z=552, 554 [M−H]$^-$.

(21) 4-[(R)-(1-phenylethyl)amino]-6-[(4-{N-[(tert-butyloxycarbonyl)methyl]-N-((S)-2-hydroxyprop-1-yl)amino}-1-oxo-2-buten-1-yl)amino]-7-methoxyquinazoline.

$R_f$ value: 0.54 (silica gel, ethyl acetate/methanol=9:1); mass spectrum (ESI$^-$): m/z=548 [M−H]$^-$.

(22) 4-[(3-chloro-4-fluorophenyl)amino]-6-[(4-{N-[(tert-butyloxycarbonyl)methyl]-N-((S)-2-hydroxyprop-1-yl)amino}-1-oxo-2-buten-1-yl)amino]-7-[(R)-(tetrahydrofuran-3-yl)oxy]quinazoline.

$R_f$ value: 0.44 (silica gel, ethyl acetate/methanol=9:1); mass spectrum (ESI$^-$): m/z=628, 630 [M−H]$^-$.

(23) 4-[(3-chloro-4-fluorophenyl)amino]-6-{[4-(5,5-dimethyl-2-oxomorpholin-4-yl)-1-oxo-2-buten-1-yl]amino}quinazoline.

Ethyl(2-hydroxy-1,1-dimethylethylamino)acetate hydrochloride is used as starting material and the cyclized product is obtained. $R_f$ value: 0.25 (silica gel, methylene chloride/methanol=15:1); mass spectrum (ESI$^-$): m/z=482, 484 [M−H]$^-$.

(24) 4-[(3-chloro-4-fluorophenyl)amino]-6-[(4-{N-[(tert-butyloxycarbonyl)methyl]-N-((R)-2-hydroxyprop-1-yl)amino}-1-oxo-2-buten-1-yl)amino]quinazoline.

$R_f$ value: 0.29 (silica gel, methylene chloride/methanol=95:5); mass spectrum (ESI$^-$): m/Z=542, 544 [M−H]$^-$.

(25) 4-[(3-chloro-4-fluorophenyl)amino]-6-[(4-{N-[(tert-butyloxycarbonyl)methyl]-N-((R)-2-hydroxyprop-1-yl)amino}-1-oxo-2-buten-1-yl)amino]-7-[(tetrahydropyran-4-yl)oxy]quinazoline.

$R_f$ value: 0.29 (silica gel, methylene chloride/methanol=95:5); mass spectrum (ESI$^-$): m/z=642, 644 [M−H]$^-$.

(26) 4-[(R)-(1-phenylethyl)amino]6-[(4-{N-[(tert-butyloxycarbonyl)methyl]-N-((S)-2-hydroxyprop-1-yl)amino}-1-oxo-2-buten-1-yl)amino]quinazoline.

$R_f$ value: 0.61 (silica gel, ethyl acetate/methanol=9:1); mass spectrum (ESI$^-$): m/z=518 [M−H]$^-$.

(27) 4-[(3-chloro-4-fluorophenyl)amino]-6-[(4-{N-[(tert-butyloxycarbonyl)methyl]-N-((R)-2-hydroxyprop-1-yl)amino}-1-oxo-2-buten-1-yl)amino]-7-cyclopentyloxyquinazoline.

$R_f$ value: 0.53 (silica gel, ethyl acetate); mass spectrum (ESI$^-$): m/z=626 [M−H]$^-$.

(28) 4-[(3-chloro-4-fluorophenyl)amino]-6-[(4-{N-[(tert-butyloxycarbonyl)methyl]-N-((R)-2hydroxyprop-1-yl)amino}-1-oxo-2-buten-1-yl)amino]-7-methoxyquinazoline.

$R_f$ value: 0.42 (silica gel, ethyl acetate/methanol=9:1); mass spectrum (ESI$^+$): m/z=574, 576 [M+H]$^+$.

(29) 4-[(R)-(1-Phenylethyl)amino]-6-[(4-{N-[(tert-butyloxycarbonyl)methyl]-N-((R)-2-hydroxyprop-1-yl)amino}-1-oxo-2-buten-1-yl)amino]quinazoline.

$R_f$ value: 0.60 (silica gel, ethyl acetate/methanol=9:1); mass spectrum (ESI$^+$): m/z=520 [M+H]$^+$.

(30) 4-[(R)-(1-Phenylethyl)amino]-6-[(4-{N-[(tert-butyloxycarbonyl)methyl]-N-((R)-2-hydroxyprop-1-yl)amino}-1-oxo-2-buten-1-yl)amino]-7-methoxyquinazoline.

$R_f$ value: 0.54 (silica gel, ethyl acetate/methanol=9:1); mass spectrum (ESI$^-$): m/z=548 [M−H]$^-$.

(31) 4-[(3-chloro-4-fluorophenyl)amino]-6-[(4-{N-[(tert-butyloxycarbonyl)methyl]-N-((R)-2-hydroxyprop-1-yl)amino}-1-oxo-2-buten-1-yl)amino]-7-[(tetrahydrofuran-3-yl)methoxy]quinazoline.

$R_f$ value: 0.41 (silica gel, ethyl acetate/methanol=9:1); mass spectrum (ESI$^+$): m/z=644, 646 [M+H]$^+$.

(32) 4-[(3-chloro-4-fluorophenyl)amino]-6-{[4-(2,2-dimethyl-6-oxomorpholin-4-yl)-1-oxo-2-buten-1-yl]amino}-7-[(tetrahydrofuran-3-yl)methoxy]quinazoline.

Ethyl(2-hydroxy-2-methylpropylamino)acetate is used as the starting material. The reaction yields the already cyclized product. $R_f$ value: 0.28 (silica gel, ethyl acetate/methanol=9:1); mass spectrum (ESI$^+$): m/z=584, 586 [M+H]$^+$.

(33) 4-[(3-chloro-4-fluorophenyl)amino]-6-{[4-(5,5-dimethyl-2-oxomorpholin-4-yl)-1-oxo-2-buten-1-yl]amino}-7-[(tetrahydrofuran-3-yl)methoxy]quinazoline.

Ethyl(2-Hydroxy-1,1-dimethylethylamino)acetate is used as the starting material. The reaction yields the already cyclized product. $R_f$ value: 0.26 (silica gel, ethyl acetate/methanol=9:1); mass spectrum (EI): m/z=583, 585 [M]$^+$.

(34) 4-[(3-chloro-4-fluorophenyl)amino]-6-[(4-{N-[(tert-butyloxycarbonyl)methyl]-N-((R)-2-hydroxyprop-1-yl)amino}-1-oxo-2-buten-1-yl)amino]-7-[(tetrahydropyran-4-yl)methoxy]quinazoline.

$R_f$ value: 0.52 (silica gel, ethyl acetate/methanol=9:1); mass spectrum (ESI$^-$): m/z=656, 658 [M−H]$^-$.

(35) 4-Benzylamino-6-[(4-{N-[(tert-butyloxycarbonyl)methyl]-N-((R)-2-hydroxyprop-1-yl)amino}-1-oxo-2-buten-1-yl)amino]-7-cyclopropylmethoxyquinazoline.

The preparation of the starting material has already been described elsewhere: WO 0051991 A1. $R_f$ value: 0.50 (silica gel, ethyl acetate/methanol=9:1); mass spectrum (ESI$^+$): m/z=576 [M+H]$^+$.

(36) 4-[(3-chloro-4-fluorophenyl)amino]-6-[(4-{N-[(tert-butyloxycarbonyl)methyl]-N-((S)-2-hydroxyprop-1-yl)amino}-1-oxo-2-buten-1-yl)amino]-7-[(tetrahydropyran-4-yl)methoxy]quinazoline.

$R_f$ value: 0.49 (aluminum oxide, ethyl acetate); mass spectrum (ESI$^+$): m/z=658, 660 [M+H]$^+$.

EXAMPLE 2

4-[(3-chloro-4-fluorophenyl)amino]-6-{[4-((S)-6-methyl-2-oxomorpholin-4-yl)-1-oxo-2-buten-1-yl]amino}-7-cyclopropylmethoxyquinazoline A mixture of 700 mg of 4-[(3-chloro-4-fluorophenyl)amino]-6-[(4-{N-[(tert-butyloxycarbonyl)methyl]-N-((S)-2-hydroxyprop-1-yl)amino}-1-oxo-2-buten-1-yl)amino]-7-cyclopropylmethoxyquinazoline and 228 mg of p-toluenesulfonic acid-hydrate in 20 ml of acetonitrile is refluxed for five hours. Then a further 200 mg of p-toluenesulfonic acid-hydrate is added and the mixture is refluxed for a further five hours. For working up, the reaction mixture is evaporated to dryness. The flask residue is divided between ethyl acetate and saturated sodium carbonate solution. The organic phase is separated off, washed with saturated sodium carbonate solution, water, and saturated sodium chloride solution, dried over magnesium sulfate, and concentrated by evaporation. The oily residue is crystallized by stirring with 15 ml of diethyl ether. Melting point: 173–175° C.; mass spectrum (ESI$^+$): m/z=540, 542 [M+H]$^+$.

The following compounds are obtained analogously to Example 2:

(1) 4-[(3-chloro-4-fluorophenyl)amino]-6-{[4-((R)-6-methyl-2-oxomorpholin-4-yl)-1-oxo-2-buten-1-yl]amino}-7-cyclopropylmethoxyquinazoline.

$R_f$ value: 0.54 (silica gel, methylene chloride/methanol=9:1); mass spectrum (ESI$^+$): m/z=540, 542 [M+H]$^+$.

(2) 4-[(3-chloro-4-fluorophenyl)amino]-6-{[4-((S)-3-methyl-2-oxomorpholin-4-yl)-1-oxo-2-buten-1-yl]amino}-7-cyclopropylmethoxyquinazoline.

The reaction is carried out with methanesulfonic acid in acetonitrile. Melting point: 182° C.; mass spectrum (ESI$^+$): m/z=540, 542 [M+H]$^+$.

(3) 4-[(3-chloro-4-fluorophenyl)amino]-6-{[4-((S)-6-methyl-2-oxomorpholin-4-yl)-1-oxo-2-buten-1-yl]amino}-7-cyclobutyloxyquinazoline.

The reaction is carried out with methanesulfonic acid in acetonitrile. $R_f$ value: 0.54 (silica gel, methylene chloride/methanol=9:1); mass spectrum (ESI$^+$): m/z=540, 542 [M+H]$^+$.

(4) 4-[(3-chloro-4-fluorophenyl)amino]-6-{[4-((R)-6-methyl-2-oxomorpholin-4-yl)-1-oxo-2-buten-1-yl]amino}-7-cyclobutyloxyquinazoline.

The reaction is carried out with methanesulfonic acid in acetonitrile. $R_f$ value: 0.54 (silica gel, methylene chloride/methanol=9:1); mass spectrum (ESI$^+$): m/z=540, 542 [M+H]$^+$.

(5) 4-[(3-chloro-4-fluorophenyl)amino]-6-{[4-((S)-6-methyl-2-oxomorpholin-4-yl)-1-oxo-2-buten-1-yl]amino}-7-[(S)-(tetrahydrofuran-3-yl)oxy]quinazoline.

The reaction is carried out with methanesulfonic acid in acetonitrile. $R_f$ value: 0.40 (silica gel, methylene chloride/methanol=9:1); mass spectrum (EI): m/z=555, 557 [M]$^+$.

(6) 4-[(3-chloro-4-fluorophenyl)amino]-6-{[4-((R)-6-methyl-2-oxomorpholin-4-yl)-1-oxo-2-buten-1-yl]amino}-7-[(S)-(tetrahydrofuran-3-yl)oxy]quinazoline.

The reaction is carried out with methanesulfonic acid in acetonitrile. $R_f$ value: 0.38 (silica gel, methylene chloride/methanol=9:1); mass spectrum (ESI$^+$): m/z=556, 558 [M+H]$^+$.

(7) 4-[(3-chloro-4-fluorophenyl)amino]-6-{[4-((R)-6-methyl-2-oxomorpholin-4-yl)-1-oxo-2-buten-1-yl]amino}-7-[(R)-(tetrahydrofuran-3-yl)oxy]quinazoline.

The reaction is carried out with methanesulfonic acid in acetonitrile. Melting point: 230° C.; mass spectrum (EI): m/z=555, 557 [M]$^+$.

(8) 4-[(3-chloro-4-fluorophenyl)amino]-6-{[4-(2,2-dimethyl-6-oxomorpholin-4-yl)-1-oxo-2-buten-1-yl]amino}-7-[(tetrahydropyran-4-yl)oxy]quinazoline.

The reaction is carried out with methanesulfonic acid in acetonitrile. $R_f$ value: 0.33 (silica gel, methylene chloride/methanol=95:5); mass spectrum (ESI$^-$): m/z=582, 584 [M−H]$^-$.

(9) 4-[(R)-(1-phenylethyl)amino]-6-{[4-((S)-6-methyl-2-oxomorpholin-4-yl)-1-oxo-2-buten-1-yl]amino}-7-methoxyquinazoline The reaction is carried out with methanesulfonic acid in acetonitrile. $R_f$ value: 0.52 (silica gel, ethyl acetate/methanol=9:1); mass spectrum (ESI$^-$): m/z=474 [M−H]$^-$.

(10) 4-[(3-chloro-4-fluorophenyl)amino]-6-{[4-((S)-6-methyl-2-oxomorpholin-4-yl)-1-oxo-2-buten-1-yl]amino}-7-[(R)-(tetrahydrofuran-3-yl)oxy]quinazoline The reaction is carried out with methanesulfonic acid in acetonitrile. $R_f$ value: 0.38 (silica gel, methylene chloride/methanol=9:1); mass spectrum (ESI$^-$): m/z=554, 556 [M−H]$^-$.

(11) 4-[(3-chloro-4-fluorophenyl)amino]-6-{[4-((R)-6-methyl-2-oxomorpholin-4-yl)-1-oxo-2-buten-1-yl]amino}quinazoline The reaction is carried out with trifluoroacetic acid in acetonitrile. $R_f$ value: 0.34 (silica gel, ethyl acetate/methanol=9:1); mass spectrum (ESI$^+$): m/z=470, 472 [M+H]$^+$.

(12) 4-[(3-chloro-4-fluorophenyl)amino]-6-{[4-((R)-6-methyl-2-oxomorpholin-4-yl)-1-oxo-2-buten-1-yl]amino}-7-[(tetrahydropyran-4-yl)oxy]quinazoline The reaction is carried out with trifluoroacetic acid in acetonitrile. $R_f$ value: 0.38 (silica gel, ethyl acetate/methanol=9:1); mass spectrum (ESI$^+$): m/z=570, 572 [M+H]$^+$.

(13) 4-[(R)-(1-phenylethyl)amino]-6-{[4-((S)-6-methyl-2-oxomorpholin-4-yl)-1-oxo-2-buten-1-yl]amino}quinazoline The reaction is carried out with trifluoroacetic acid in acetonitrile. $R_f$ value: 0.50 (silica gel, ethyl acetate/methanol=9:1); mass spectrum (ESI$^-$): m/z=444 [M−H]$^-$.

(14) 4-[(3-chloro-4-fluorophenyl)amino]-6-{[4-((R)-6-methyl-2-oxomorpholin-4-yl)-1-oxo-2-buten-1-yl]amino}-7-cyclopentyloxyquinazoline $R_f$ value: 0.38 (silica gel, ethyl acetate); mass spectrum (ESI$^+$): m/z=554, 556 [M+H]$^+$.

(15) 4-[(3-chloro-4-fluorophenyl)amino]-6-{[4-((R)-6-methyl-2-oxomorpholin-4-yl)-1-oxo-2-buten-1-yl]amino}-7-methoxyquinazoline $R_f$ value: 0.13 (silica gel, ethyl acetate/methanol=9:1); mass spectrum (ESI$^+$): m/z=500, 502 [M+H]$^+$.

(16) 4-[(R)-(1-Phenylethyl)amino]-6-{[4-((R)-6-methyl-2-oxomorpholin-4-yl)-1-oxo-2-buten-1-yl]amino}quinazoline $R_f$ value: 0.34 (silica gel, ethyl acetate/methanol=9:1); mass spectrum (ESI$^+$): m/z=446 [M+H]$^+$.

(17) 4-[(R)-(1-Phenylethyl)amino]-6-{[4-((R)-6-methyl-2-oxomorpholin-4-yl)-1-oxo-2-buten-1-yl]amino}-7-methoxyquinazoline $R_f$ value: 0.48 (silica gel, ethyl acetate/methanol=4:1); mass spectrum (ESI$^+$): m/z=476 [M+H]$^+$.

(18) 4-[(3-chloro-4-fluorophenyl)amino]-6-{[4-((R)-6-methyl-2-oxomorpholin-4-yl)-1-oxo-2-buten-1-yl]amino}-7-[(tetrahydrofuran-3-yl)methoxy]quinazoline $R_f$ value: 0.48 (silica gel, ethyl acetate/methanol=4:1); mass spectrum (ESI$^-$): m/z=568, 570 [M−H]$^-$.

(19) 4-[(3-chloro-4-fluorophenyl)amino]-6-{[4-((R)-6-methyl-2-oxomorpholin-4-yl)-1-oxo-2-buten-1-yl]amino}-7-[(tetrahydropyran-4-yl)methoxy]quinazoline Melting point: 196° C.; mass spectrum (ESI$^+$): m/z=584, 586 [M+H]$^+$.

(20) 4-Benzylamino-6-{[4-((R)-6-methyl-2-oxomorpholin-4-yl)-1-oxo-2-buten-1-yl]amino}-7-cyclopropylmethoxyquinazoline.

$R_f$ value: 0.41 (silica gel, ethyl acetate/methanol=9:1); mass spectrum (ESI$^+$): m/z=502 [M+H]$^+$.

(21) 4-[(3-chloro-4-fluorophenyl)amino]-6-{[4-((S)-6-methyl-2-oxomorpholin-4-yl)-1-oxo-2-buten-1-yl]amino}-7-[(tetrahydropyran-4-yl)methoxy]quinazoline Melting point: 196–199° C.; mass spectrum (ESI$^+$): m/z=584, 586 [M+H]$^+$.

EXAMPLE 3

4-[(3-chloro-4-fluorophenyl)amino]-6-({4-[N-(carboxymethyl)-N-((R)-2-hydroxyprop-1-yl)amino]-1-oxo-2-buten-1-yl}amino)-7-cyclopropylmethoxyquinazoline 100 mg of 4-[(3-chloro-4-fluorophenyl)amino]-6-{[4-((R)-6-methyl-2-oxomorpholin-4-yl)-1-oxo-2-buten-1-yl]amino}-7-cyclopropylmethoxyquinazoline is mixed with 1.63 ml of water and 0.37 ml of 1N hydrochloric acid. The reaction mixture is stirred for three hours at 60° C. and then left to stand overnight at ambient temperature. For working up, 0.37 ml 1N sodium hydroxide solution is added and the mixture is cooled in an ice bath, whereupon a light-colored precipitate is deposited. This is suction filtered, washed with cold water, and dried. Yield: 60 mg (58% of theory); mass spectrum (ESI⁻): m/z=556, 558 [M–H]⁻.

The following compounds are obtained analogously to Example 3:

(1) 4-[(3-chloro-4-fluorophenyl)amino]-6-({4-[N-(carboxymethyl)-N-(2-hydroxy-2-methylprop-1-yl)amino]-1-oxo-2-buten-1-yl}amino)-7-cyclopropylmethoxyquinazoline.

The preparation of the starting material has already been described elsewhere: WO 0051991 A1. $R_f$ value: 0.62 (Reversed phase ready-made TLC plate (E. Merck), acetonitrile/water/trifluoroacetic acid=50:50:1); mass spectrum (ESI⁻): m/z=570, 572 [M–H]⁻.

(2) 4-[(3-chloro-4-fluorophenyl)amino]-6-({4-[N-(carboxymethyl)-N-(1,1-dimethyl-2-hydroxyethyl)amino]-1-oxo-2-buten-1-yl}amino)-7-cyclopropylmethoxyquinazoline.

The preparation of the starting material has already been described elsewhere: WO 0051991 A1. Melting point: 163° C.–166° C.; mass spectrum (ESI⁻): m/z=570, 572 [M–H]⁻.

EXAMPLE 4

4-[(3-chloro-4-fluorophenyl)amino]-6-[(4-{N-[(methoxycarbonyl)methyl]-N-((R)-2-hydroxyprop-1-yl)amino}-1-oxo-2-buten-1-yl)amino]-7-cyclopropylmethoxy quinazoline Obtained by treating a methanolic solution of 4-[(3-chloro-4-fluorophenyl)amino]-6-{[4-((R)-6-methyl-2-oxomorpholin-4-yl)-1-oxo-2-buten-1-yl]amino}-7-cyclopropylmethoxyquinazoline with ethereal hydrochloric acid at room temperature. $R_f$ value: 0.37 (silica gel, methylene chloride/methanol=20:1); mass spectrum (ESI⁻): m/z=570, 572 [M–H]⁻.

The following compounds may also be obtained analogously to the above Examples and other methods known from the literature:

(1) 4-[(3-bromophenyl)amino]-6-{[4-((S)-3-methyl-2-oxomorpholin-4-yl)-1-oxo-2-buten-1-yl]amino}quinazoline.

(2) 4-[(3-bromophenyl)amino]-6-{[4-((R)-6-methyl-2-oxomorpholin-4-yl)-1-oxo-2-buten-1-yl]amino}quinazoline.

(3) 4-[(3-bromophenyl)amino]-6-{[4-(5,5-dimethyl-2-oxomorpholin-4-yl)-1-oxo-2-buten-1-yl]amino}quinazoline.

(4) 4-[(3-methylphenyl)amino]-6-{[4-((S)-3-methyl-2-oxomorpholin-4-yl)-1-oxo-2-buten-1-yl]amino}quinazoline.

(5) 4-[(3-methylphenyl)amino]-6-{[4-((R)-6-methyl-2-oxomorpholin-4-yl)-1-oxo-2-buten-1-yl]amino}quinazoline.

(6) 4-[(3-methylphenyl)amino]-6-{[4-(5,5-dimethyl-2-oxomorpholin-4-yl)-1-oxo-2-buten-1-yl]amino}quinazoline.

(7) 4-[(3-ethynylphenyl)amino]-6-{[4-((S)-3-methyl-2-oxomorpholin-4-yl)-1-oxo-2-buten-1-yl]amino}quinazoline.

(8) 4-[(3-ethynylphenyl)amino]-6-{[4-((R)-6-methyl-2-oxomorpholin-4-yl)-1-oxo-2-buten-1-yl]amino}quinazoline.

(9) 4-[(3-ethynylphenyl)amino]-6-{[4-(5,5-dimethyl-2-oxomorpholin-4-yl)-1-oxo-2-buten-1-yl]amino}quinazoline.

(10) 4-[(3-chloro-4-fluorophenyl)amino]-6-{[4-((S)-3-methyl-2-oxomorpholin-4-yl)-1-oxo-2-buten-1-yl]amino}quinazoline.

(11) 4-[(3-chloro-4-fluorophenyl)amino]-6-{[4-((S)-3-methyl-2-oxomorpholin-4-yl)-1-oxo-2-buten-1-yl]amino}-7-methoxyquinazoline.

(12) 4-[(3-chloro-4-fluorophenyl)amino]-6-{[4-((S)-3-methyl-2-oxomorpholin-4-yl)-1-oxo-2-buten-1-yl]amino}-7-(2-methoxyethoxy)quinazoline.

(13) 4-[(3-chloro-4-fluorophenyl)amino]-6-{[4-((S)-3-methyl-2-oxomorpholin-4-yl)-1-oxo-2-buten-1-yl]amino}-7-[(R)-(tetrahydrofuran-3-yl)oxy]quinazoline.

(14) 4-[(3-chloro-4-fluorophenyl)amino]-6-{[4-((S)-3-methyl-2-oxomorpholin-4-yl)-1-oxo-2-buten-1-yl]amino}-7-[(S)-(tetrahydrofuran-3-yl)oxy]quinazolin.

(15) 4-[(3-chloro-4-fluorophenyl)amino]-6-{[4-((S)-3-methyl-2-oxomorpholin-4-yl)-1-oxo-2-buten-1-yl]amino}-7-[(R)-(tetrahydrofuran-2-yl)methoxy]quinazoline.

(16) 4-[(3-chloro-4-fluorophenyl)amino]-6-{[4-((S)-3-methyl-2-oxomorpholin-4-yl)-1-oxo-2-buten-1-yl]amino}-7-[(S)-(tetrahydrofuran-2-yl)methoxy]quinazoline.

(17) 4-[(3-chloro-4-fluorophenyl)amino]-6-{[4-((R)-6-methyl-2-oxomorpholin-4-yl)-1-oxo-2-buten-1-yl]amino}-7-[(tetrahydrofuran-3-yl)methoxy]quinazoline.

(18) 4-[(3-chloro-4-fluorophenyl)amino]-6-{[4-((R)-6-methyl-2-oxomorpholin-4-yl)-1-oxo-2-buten-1-yl]amino}-7-[(tetrahydropyran-4-yl)methoxy]quinazoline.

(19) 4-[(3-chloro-4-fluorophenyl)amino]-6-{[4-((R)-6-methyl-2-oxomorpholin-4-yl)-1-oxo-2-buten-1-yl]amino}-7-[(tetrahydropyran-2-yl)methoxy]quinazoline.

(20) 4-[(3-trifluoromethylphenyl)amino]-6-{[4-((R)-6-methyl-2-oxomorpholin-4-yl)-1-oxo-2-buten-1-yl]amino}-7-methoxyquinazoline.

(21) 4-[(3-cyanophenyl)amino]-6-{[4-((R)-6-methyl-2-oxomorpholin-4-yl)-1-oxo-2-buten-1-yl]amino}-7-methoxyquinazoline.

(22) 4-[(3-chloro-4-fluorophenyl)amino]-6-{[4-((R)-6-methyl-2-oxomorpholin-4-yl)-1-oxo-2-buten-1-yl]amino}quinazoline.

(23) 4-[(3-chloro-4-fluorophenyl)amino]-6-{[4-((R)-6-methyl-2-oxomorpholin-4-yl)-1-oxo-2-buten-1-yl]amino}-7-methoxyquinazoline.

(24) 4-[(3-chloro-4-fluorophenyl)amino]-6-{[4-((R)-6-methyl-2-oxomorpholin-4-yl)-1-oxo-2-buten-1-yl]amino}-7-(2-methoxyethoxy)quinazoline.

(25) 4-[(3-chloro-4-fluorophenyl)amino]-6-{[4-((R)-6-methyl-2-oxomorpholin-4-yl)-1-oxo-2-buten-1-yl]amino}-7-[(tetrahydropyran-4-yl)oxy]quinazoline.

(26) 4-[(3-chloro-4-fluorophenyl)amino]-6-{[4-((R)-6-methyl-2-oxomorpholin-4-yl)-1-oxo-2-buten-1-yl]amino}-7-[(R)-(tetrahydrofuran-2-yl)methoxy]quinazoline.

(27) 4-[(3-chloro-4-fluorophenyl)amino]-6-{[4-((R)-6-methyl-2-oxomorpholin-4-yl)-1-oxo-2-buten-1-yl]amino}-7-[(S)-(tetrahydrofuran-2-yl)methoxy]quinazoline.

(28) 4-[(R)-(1-phenylethyl)amino]-6-{[4-((R)-6-methyl-2-oxomorpholin-4-yl)-1-oxo-2-buten-1-yl]amino}quinazoline.
(29) 4-[(R)-(1-phenylethyl)amino]-6-{[4-((S)-3-methyl-2-oxomorpholin-4-yl)-1-oxo-2-buten-1-yl]amino}quinazoline.
(30) 4-[(R)-(1-phenylethyl)amino]-6-{[4-((S)-3-methyl-2-oxomorpholin-4-yl)-1-oxo-2-buten-1-yl]amino}-7-methoxyquinazoline.
(31) 4-[(R)-(1-phenylethyl)amino]-6-{[4-((R)-6-methyl-2-oxomorpholin-4-yl)-1-oxo-2-buten-1-yl]amino}-7-methoxyquinazoline.
(32) 4-[(3-chloro-4-fluorophenyl)amino]-6-{[4-((S)-3-methyl-2-oxomorpholin-4-yl)-1-oxo-2-buten-1-yl]amino}-7-ethoxyquinazoline.
(33) 4-[(3-chloro-4-fluorophenyl)amino]-6-{[4-((R)-6-methyl-2-oxomorpholin-4-yl)-1-oxo-2-buten-1-yl]amino}-7-ethoxyquinazoline.

EXAMPLE 5

Coated Tablets Containing 75 mg of Active Substance

| Component | Amount per tablet core (mg) |
| --- | --- |
| active substance | 75 |
| calcium phosphate | 93.0 |
| corn starch | 35.5 |
| polyvinylpyrrolidone | 10.0 |
| hydroxypropylmethylcellulose | 15.0 |
| magnesium stearate | 1.5 |
| TOTAL | 230.0 |

Preparation

The active substance is mixed with calcium phosphate, corn starch, polyvinylpyrrolidone, hydroxypropylmethylcellulose, and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape. Weight of core: 230 mg; die: 9 mm, convex. The tablet cores thus produced are coated with a film consisting essentially of hydroxypropylmethylcellulose. The finished film-coated tablets are polished with beeswax. Weight of coated tablet: 245 mg.

EXAMPLE 6

Tablets Containing 100 mg of Active Substance

| Component | Amount per tablet (mg) |
| --- | --- |
| active substance | 100.0 |
| lactose | 80.0 |
| corn starch | 34.0 |
| polyvinylpyrrolidone | 4.0 |
| magnesium stearate | 2.0 |
| TOTAL | 220.0 |

Preparation

The active substance, lactose, and starch are mixed together and uniformly moistened with an aqueous solution of the polyvinylpyrrolidone. After the moist composition has been screened (2.0 mm mesh size) and dried in a rack-type drier at 50° C., it is screened again (1.5 mm mesh size) and the lubricant is added. The finished mixture is compressed to form tablets. Weight of tablet: 220 mg; diameter: 10 mm, biplanar, facetted on both sides and notched on one side.

EXAMPLE 7

Tablets Containing 150 mg of Active Substance

| Component | Amount per tablet (mg) |
| --- | --- |
| active substance | 150.0 |
| powdered lactose | 89.0 |
| corn starch | 40.0 |
| colloidal silica | 10.0 |
| polyvinylpyrrolidone | 10.0 |
| magnesium stearate | 1.0 |
| TOTAL | 300.0 |

Preparation

The active substance mixed with lactose, corn starch, and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture. Weight of tablet: 300 mg; die: 10 mm, flat.

EXAMPLE 8

Hard Gelatine Capsules Containing 150 mg of Active Substance

| Component | Amount per capsule (mg) |
| --- | --- |
| active substance | 150.0 |
| corn starch (dried) | approx. 80.0 |
| lactose (powdered) | approx. 87.0 |
| magnesium stearate | 3.0 |
| TOTAL | 320.0 |

Preparation

The active substance is mixed with the excipients, passed through a screen with a mesh size of 0.75 mm and homogeneously mixed using a suitable apparatus. The finished mixture is packed into size 1 hard gelatine capsules. Capsule filling: approx. 320 mg; capsule shell: size 1 hard gelatine capsule.

EXAMPLE 9

Suppositories Containing 150 mg of Active Substance

| Component | Amount per suppository (mg) |
| --- | --- |
| active substance | 150.0 |
| polyethyleneglycol 1500 | 550.0 |
| polyethyleneglycol 6000 | 460.0 |
| polyoxyethylene sorbitan monostearate | 840.0 |
| TOTAL | 2000.0 |

Preparation

After the suppository mass has been melted, the active substance is homogeneously distributed therein and the melt is poured into chilled molds.

EXAMPLE 10

| Suspension Containing 50 mg of Active Substance/5 ml | |
|---|---|
| Component | Amount/100 ml suspension |
| active substance | 1.0 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavoring | 0.30 g |
| distilled water | ad 100 ml |

Preparation

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution, and the flavoring have been added and dissolved, the suspension is evacuated with stirring to eliminate air. 5 ml of suspension contains 50 mg of active substance.

EXAMPLE 11

| Ampoules Containing 10 mg of Active Substance | |
|---|---|
| Component | Amount |
| active substance | 10.0 mg |
| 0.01 N hydrochloric acid | q.s. |
| double-distilled water | ad 2.0 ml |

Preparation

The active substance is dissolved in the necessary amount of 0.01N HCl, made isotonic with common salt, filtered sterile, and transferred into 2 ml ampoules.

EXAMPLE 12

| Ampoules Containing 50 mg of Active Substance | |
|---|---|
| Component | Amount |
| active substance | 50.0 mg |
| 0.01 N hydrochloric acid | q.s. |
| double-distilled water | ad 10.0 ml |

Preparation

The active substance is dissolved in the necessary amount of 0.01N HCl, made isotonic with common salt, filtered sterile, and transferred into 10 ml ampoules.

EXAMPLE 13

| Capsules for Powder Inhalation Containing 5 mg of Active Substance | |
|---|---|
| Component | Amount per capsule (mg) |
| active substance | 5.0 |
| lactose for inhalation | 15.0 |
| TOTAL | 20.0 |

Preparation

The active substance is mixed with lactose for inhalation. The mixture is packed into capsules in a capsule-making machine (weight of the empty capsule approx. 50 mg). Weight of capsule: 70.0 mg; size of capsule: 3.

EXAMPLE 14

| Solution for Inhalation for Hand-Held Nebulisers Containing 2.5 mg of Active Substance | |
|---|---|
| Component | Amount per spray |
| active substance | 2.500 mg |
| benzalkonium chloride | 0.001 mg |
| 1N hydrochloric acid | q.s. |
| ethanol/water (50/50) | ad 15.000 mg |

Preparation

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges). Contents of the container: 4.5 g.

We claim:

1. A compound of formula (I)

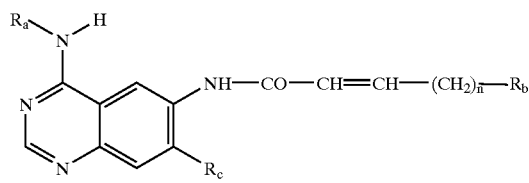

wherein:

$R_a$ is a benzyl or 1-phenylethyl group or a phenyl group substituted by the groups $R_1$ and $R_2$, wherein:

$R_1$ is a hydrogen, fluorine, chlorine, or bromine atom, or a methyl, trifluoromethyl, cyano, or ethynyl group, and $R_2$ is a hydrogen or fluorine atom;

$R_b$ is an $R_3O$—CO—$CH_2$—N—$CH_2$—$CH_2$—OH group optionally substituted at the methylene groups by 1 or 2 methyl or ethyl groups, wherein $R_3$ is a hydrogen atom or a $C_{1-4}$-alkyl group, a 2-oxomorpholin-4-yl group optionally substituted by 1 or 2 methyl or ethyl groups, or a N-[(1,3-dioxolan-2-yl)methyl]methylamino group;

R_c is a hydrogen atom, or a methoxy, ethoxy, 2-methoxyethoxy, 2-ethoxyethoxy, cyclobutyloxy, cyclopentyloxy, cyclohexyloxy, cyclopropylmethoxy, cyclobutylmethoxy, cyclopentylmethoxy, cyclohexylmethoxy, tetrahydrofuran-3-yloxy, tetrahydropyran-3-yloxy, tetrahydropyran-4-yloxy, tetrahydrofuranylmethoxy, or tetrahydropyranylmethoxy group; and n is 1, 2, or 3, or a tautomer, stereoisomer, or salt thereof, with the proviso that the following compounds are excluded:

4-[(3-bromophenyl)amino]-6-({4-[N-(1,3-dioxolan-2-ylmethyl)-N-methylamino]-1-oxo-2-buten-1-yl}amino)-7-methoxyquinazoline;

4-[(3-bromophenyl)amino]-6-{[4-(2-oxomorpholin-4-yl)-1-oxo-2-buten-1-yl]amino}-7-methoxyquinazoline;

4-[(3-bromophenyl)amino]-6-[(4-{N-[(tert-butyloxycarbonyl)methyl]-N-(2-hydroxyethyl)amino}-1-oxo-2-buten-1-yl)amino]-7-methoxyquinazoline;

4-[(3-bromophenyl)amino]-6-({4-[N-(carboxymethyl)-N-(2-hydroxyethyl)amino]-1-oxo-2-buten-1-yl}amino)-7-methoxyquinazoline;

4-[(3-chloro-4-fluorophenyl)amino]-6-{[4-(2-oxomorpholin-4-yl)-1-oxo-2-buten-1-yl]amino}-7-cyclopropylmethoxyquinazoline;

4-[(3-chloro-4-fluorophenyl)amino]-6-[(4-{N-[(ethoxycarbonyl)methyl]-N-(2-hydroxyethyl)amino}-1-oxo-2-buten-1-yl)amino]-7-cyclopropylmethoxyquinazoline;

4-[(3-chloro-4-fluorophenyl)amino]-6-[(4-{N-[(ethoxycarbonyl)methyl]-N-(2-hydroxy-2-methylpropyl)amino}-1-oxo-2-buten-1-yl)amino]-7-cyclopropylmethoxyquinazoline;

4-[(3-chloro-4-fluorophenyl)amino]-6-{[4-(2,2-dimethyl-6-oxomorpholin-4-yl)-1-oxo-2-buten-1-yl]amino}-7-cyclopropylmethoxyquinazoline;

4-[(3-chloro-4-fluorophenyl)amino]-6-{[4-(5,5-dimethyl-2-oxomorpholin-4-yl)-1-oxo-2-buten-1-yl]amino}-7-cyclopropylmethoxyquinazoline;

4-[(3-chloro-4-fluorophenyl)amino]-6-{[4-(5-methyl-2-oxomorpholin-4-yl)-1-oxo-2-buten-1-yl]amino}-7-cyclopropylmethoxyquinazoline;

(R)-4-[(3-chloro-4-fluorophenyl)amino]-6-[(4-{N-[1-(ethoxycarbonyl)ethyl]-N-(2-hydroxyethyl)amino}-1-oxo-2-buten-1-yl)amino]-7-cyclopropylmethoxyquinazoline;

(R)-4-[(3-chloro-4-fluorophenyl)amino]-6-{[4-(3-methyl-2-oxomorpholin-4-yl)-1-oxo-2-buten-1-yl]amino}-7-cyclopropylmethoxyquinazoline;

4-[(3-chloro-4-fluorophenyl)amino]-6-[(4[N-(1,3-dioxolan-2-ylmethyl)-N-methylamino[-1-oxo-2-buten-1yl)amino]-7-cyclopropylmethoxyquinazoline;

4-(3-chloro-4-fluorophenyl)amino]-6-{[4-(3-methyl-2-oxomorpholin-4-yl)-1-oxo-2-buten-1-yl]amino}-7-cyclopropylmethoxyquinazoline; and 4-[(3-chloro-4-fluorophenyl)amino]-6-{[4-(6-methyl-2-oxomorpholin-4-yl)-1-oxo-2-buten-1-yl]amino}-7-cyclopropylmethoxyquinazoline.

2. A compound of formula (I) according to claim 1, wherein:

$R_a$ is a benzyl or 1-phenylethyl group or a phenyl group substituted by the groups $R_1$ and $R_2$, wherein:
  $R_1$ is a fluorine, chlorine, or bromine atom, or a methyl or ethynyl group, and
  $R_2$ is a hydrogen or fluorine atom, $R_b$ is an $R_3O-CO-CH_2-N-CH_2-CH_2-OH$ group substituted at the methylene groups by 1 or 2 methyl or ethyl groups, wherein $R_3$ is a $C_{1-4}$-alkyl group, or a 2-oxomorpholin-4-yl group substituted by 1 or 2 methyl or ethyl groups;

$R_c$ is a hydrogen atom, or a methoxy, ethoxy, 2-methoxyethoxy, cyclobutyloxy, cyclopentyloxy, cyclopropylmethoxy, cyclobutylmethoxy, tetrahydrofuran-3-yloxy, tetrahydropyran-4-yloxy, tetrahydrofuranylmethoxy, or tetrahydropyranylmethoxy group; and n is 1 or 2, or a tautomer, stereoisomer, or salt thereof.

3. A compound of formula (I) according to claim 1, wherein:

$R_a$ is a benzyl or 1-phenylethyl group or a phenyl group substituted by the groups $R_1$ and $R_2$, wherein $R_1$ is a fluorine, chlorine, or bromine atom, and $R_2$ is a hydrogen or fluorine atom;

$R_b$ is a 2-oxomorpholin-4-yl group substituted by 1 or 2 methyl or ethyl groups;

$R_c$ is a hydrogen atom, or a methoxy, ethoxy, 2-methoxyethoxy, cyclobutyloxy, cyclopentyloxy, cyclopropylmethoxy, tetrahydrofuran-3-yloxy, tetrahydropyran-4-yloxy, tetrahydrofuranylmethoxy, or tetrahydropyranylmethoxy group; and n is 1, or a tautomer, stereoisomer, or salt thereof.

4. A compound of formula (I) according to claim 1, wherein:

$R_a$ is a 1-phenylethyl or a 3-chloro-4-fluorophenyl group;

$R_b$ is a 2-oxomorpholin-4-yl group substituted by 1 or 2 methyl groups, or
  a 2-oxomorpholin-4-yl group substituted by an ethyl group;

$R_c$ is a hydrogen atom, or a methoxy, 2-methoxyethoxy, cyclobutyloxy, cyclopentyloxy, cyclopropylmethoxy, tetrahydrofuran-3-yloxy, tetrahydropyran-4-yloxy, tetrahydrofuranylmethoxy, or tetrahydropyranylmethoxy group; and n is 1, or a tautomer, stereoisomer, or salt thereof.

5. A compound selected from the group consisting of:

(a) 4-[(3-chloro-4-fluorophenyl)amino]-6-{[4-((S)-6-methyl-2-oxomorpholin-4-yl)-1-oxo-2-buten-1-yl]amino}-7-cyclopropylmethoxyquinazoline;

(b) 4-[(3-chloro-4-fluorophenyl)amino]-6-{[4-((R)-6-methyl-2-oxomorpholin-4-yl)-1-oxo-2-buten-1-yl]amino}-7-cyclopropylmethoxyquinazoline;

(c) 4-[(3-chloro-4-fluorophenyl)amino]-6-{[4-((S)-3-methyl-2-oxomorpholin-4-yl)-1-oxo-2-buten-1-yl]amino}-7-cyclopropylmethoxyquinazoline;

(d) 4-[(3-chloro-4-fluorophenyl)amino]-6-{[4-(5,5-dimethyl-2-oxomorpholin-4-yl)-1-oxo-2-buten-1-yl]amino}-7-(2-methoxyethoxy)quinazoline;

(e) 4-[(3-chloro-4-fluorophenyl)amino]-6-{[4-((S)-6-methyl-2-oxomorpholin-4-yl)-1-oxo-2-buten-1-yl]amino}-7-cyclobutyloxyquinazoline;

(f) 4-[(3-chloro-4-fluorophenyl)amino]-6-{[4-((R)-6-methyl-2-oxomorpholin-4-yl)-1-oxo-2-buten-1-yl]amino}-7-cyclobutyloxyquinazoline;

(g) 4-[(3-chloro-4-fluorophenyl)amino]-6-{[4-(5,5-dimethyl-2-oxomorpholin-4-yl)-1-oxo-2-buten-1-yl]amino}-7-cyclobutyloxyquinazoline;

(h) 4-[(3-chloro-4-fluorophenyl)amino]-6-{[4-(5,5-dimethyl-2-oxomorpholin-4-yl)-1-oxo-2-buten-1-yl]amino}-7-cyclopentyloxyquinazoline;

(i) 4-[(R)-(1-phenylethyl)amino]-6-{[4-(5,5-dimethyl-2-oxomorpholin-4-yl)-1-oxo-2-buten-1-yl]amino}quinazoline;

(j) 4-[(3-chloro-4-fluorophenyl)amino]-6-{[4-(5,5-dimethyl-2-oxomorpholin-4-yl)-1-oxo-2-buten-1-yl]amino}-7-[(R)-(tetrahydrofuran-3-yl)oxy]quinazoline;

(k) 4-[(3-chloro-4-fluorophenyl)amino]-6-{[4-((S)-6-methyl-2-oxomorpholin-4-yl)-1-oxo-2-buten-1-yl]amino}-7-[(S)-(tetrahydrofuran-3-yl)oxy]quinazoline;

(l) 4-[(3-chloro-4-fluorophenyl)amino]-6-{[4-((R)-6-methyl-2-oxomorpholin-4-yl)-1-oxo-2-buten-1-yl]amino}-7-[(S)-(tetrahydrofuran-3-yl)oxy]quinazoline;

(m) 4-[(3-chloro-4-fluorophenyl)amino]-6-{[4-((R)-6-methyl-2-oxomorpholin-4-yl)-1-oxo-2-buten-1-yl]amino}-7-[(R)-(tetrahydrofuran-3-yl)oxy]quinazoline;

(n) 4-[(3-chloro-4-fluorophenyl)amino]-6-{[4-(5,5-dimethyl-2-oxomorpholin-4-yl)-1-oxo-2-buten-1-yl]amino}-7-[(tetrahydropyran-4-yl)oxy]quinazoline;

(o) 4-[(R)-(1-phenylethyl)amino]-6-{[4-(5,5-dimethyl-2-oxomorpholin-4-yl)-1-oxo-2-buten-1-yl]amino}-7-cyclopropylmethoxyquinazoline;

(p) 4-[(3-chloro-4-fluorophenyl)amino]-6-{[4-(2,2-dimethyl-6-oxomorpholin-4-yl)-1-oxo-2-buten-1-yl]amino}-7-[(tetrahydropyran-4-yl)oxy]quinazoline;

(q) 4-[(3-chloro-4-fluorophenyl)amino]-6-{[4-(5,5-dimethyl-2-oxomorpholin-4-yl)-1-oxo-2-buten-1-yl]amino}-7-methoxyquinazoline;

(r) 4-[(3-chloro-4-fluorophenyl)amino]-6-{[4-(5,5-dimethyl-2-oxomorpholin-4-yl)-1-oxo-2-buten-1-yl]amino}-7-[(tetrahydrofuran-2-yl)methoxy]quinazoline;

(s) 4-[(3-chloro-4-fluorophenyl)amino]-6-{[4-(5,5-dimethyl-2-oxomorpholin-4-yl)-1-oxo-2-buten-1-yl]amino}-7-[(S)-(tetrahydrofuran-3-yl)oxy]quinazoline;

(t) 4-[(3-chloro-4-fluorophenyl)amino]-6-{[4-(6-ethyl-2-oxomorpholin-4-yl)-1-oxo-2-buten-1-yl]amino}-7-cyclopropylmethoxyquinazoline;

(u) 4-[(R)-(1-phenylethyl)amino]-6-{[4-((S)-6-methyl-2-oxomorpholin-4-yl)-1-oxo-2-buten-1-yl]amino}-7-methoxyquinazoline;

(v) 4-[(3-chloro-4-fluorophenyl)amino]-6-{[4-((S)-6-methyl-2-oxomorpholin-4-yl)-1-oxo-2-buten-1-yl]amino}-7-[(R)-(tetrahydrofuran-3-yl)oxy]quinazoline;

(w) 4-[(3-chloro-4-fluorophenyl)amino]-6-{[4-(5,5-dimethyl-2-oxomorpholin-4-yl)-1-oxo-2-buten-1-yl]amino}quinazoline;

(x) 4-[(3-chloro-4-fluorophenyl)amino]-6-{[4-((R)-6-methyl-2-oxomorpholin-4-yl)-1-oxo-2-buten-1-yl]amino}quinazoline;

(y) 4-[(3-chloro-4-fluorophenyl)amino]-6-{[4-((R)-6-methyl-2-oxomorpholin-4-yl)-1-oxo-2-buten-1-yl]amino}-7-[(tetrahydropyran-4-yl)oxy]quinazoline; and (z) 4-[(R)-(1-phenylethyl)amino]-6-{[4-((S)-6-methyl-2-oxomorpholin-4-yl)-1-oxo-2-buten-1-yl]amino}quinazoline, and the tautomers, stereoisomers, and salts thereof.

6. The compound according to one of claims 1 to 5 wherein the compound is a physiologically acceptable salt.

7. A pharmaceutical composition comprising an effective amount of a compound of formula (I) according to one of claims 1 to 5 and an inert carrier or diluent.

8. A pharmaceutical composition comprising an effective amount of a compound of formula (I) according to one of claim 5 an inert carrier or diluent.

* * * * *